United States Patent
Corbin

(10) Patent No.: US 11,692,167 B2
(45) Date of Patent: Jul. 4, 2023

(54) CHEMICALLY DEFINED SERUM REPLACEMENTS FOR CELL CULTURE

(71) Applicant: Montana State University, Bozeman, MT (US)

(72) Inventor: Elizabeth Dale Corbin, Bozeman, MT (US)

(73) Assignee: MONTANA STATE UNIVERSITY, Bozeman, MT (US)

( * ) Notice: Subject to any disclaimer, the term of this patent is extended or adjusted under 35 U.S.C. 154(b) by 0 days.

(21) Appl. No.: 17/879,390

(22) Filed: Aug. 2, 2022

(65) Prior Publication Data

US 2023/0052904 A1 Feb. 16, 2023

Related U.S. Application Data

(60) Provisional application No. 63/228,328, filed on Aug. 2, 2021.

(51) Int. Cl.
*C12N 5/00* (2006.01)

(52) U.S. Cl.
CPC ........ *C12N 5/0037* (2013.01); *C12N 2500/10* (2013.01); *C12N 2500/32* (2013.01); *C12N 2500/36* (2013.01); *C12N 2500/38* (2013.01); *C12N 2500/90* (2013.01); *C12N 2501/105* (2013.01); *C12N 2501/11* (2013.01)

(58) Field of Classification Search
CPC .............. C12N 5/0037; C12N 2500/10; C12N 2500/32; C12N 2500/36; C12N 2500/38; C12N 2500/90; C12N 2501/105; C12N 2501/11
See application file for complete search history.

(56) References Cited

U.S. PATENT DOCUMENTS

2007/0292949 A1 12/2007 Duguay et al.
2010/0098725 A1 4/2010 Liu et al.

FOREIGN PATENT DOCUMENTS

WO 2009/055853 A1 3/2019

OTHER PUBLICATIONS

Corbin, E., Complexation of lipids with cyclodextrin carriers for fully defined supplementation of cell culture. Montana State Univ., Dissertation, Apr. 2019 [retrieved Dec. 12, 2022]. <URL: https://scholarworks.montana.edu/xmlui/bitstream/handle/1/16182/corbin-complexation-of-2019.pdf?sequence=1&isAllowed> (Year: 2019).*
Transferrin in cell culture. Datasheet, Sigma [retrieved Dec. 13, 2022]. Retrieved from the Internet:<URL: https://www.sigmaaldrich.com/US/en/technical-documents/technical-article/cell-culture-and-cell-culture-analysis/mammalian-cell-culture/transferrin> (Year: 2022).*
Corbin, Complexation of Lipids with Cyclodextrin Carriers for Fully Defined Supplementation of Cell Culture, Montana State University, Dissertation, Apr. 2019 [retrieved Sep. 19, 2022]. Retrieved from the internet: <URL: https://scholarworks.montana.edu/xmlui/bitstream/handle/1/16182/corbin-complexation-of-2019.pdf? sequence=I&isAllowed=y>, pp. i-x, abstract. 72-83, 100-104.
International Search Report of PCT/US22/39165 dated Sep. 22, 2022.
The First Targeted Delivery of siRNA in Humans via a Self-Assembling, Cyclodextrin Polymer-Based Nanoparticle: From Concept to Clinic; Mark E. Davis; Chemical Engineering, California Institute of Technology, Pasadena, California 91125; Received Jan. 15, 2009; Revised Manuscript Received Mar. 3, 2009; Accepted Mar. 6, 2009.

* cited by examiner

*Primary Examiner* — Kara D Johnson
(74) *Attorney, Agent, or Firm* — Polsinelli PC

(57) ABSTRACT

Disclosures herein are directed to chemically defined animal-derived component free supplements designed for individual cell types that supports the ex vivo growth of cells as well or better than serum, in chemically defined conditions.

18 Claims, 6 Drawing Sheets

| Lipid | Estimated Free Lipid Concentration in MBCD | Critical Micelle Concentration from Literature |
|---|---|---|
| DHA | 36μM | 100μM |
| Palmitoleic Acid | 74μM | 150μM |
| Cholesterol Sulfate | 0.5μM | 0.5μM |
| Oleic Acid | 60μM | 6μM |
| A Linolenic Acid | 68μM | 150μM |
FIG. 7
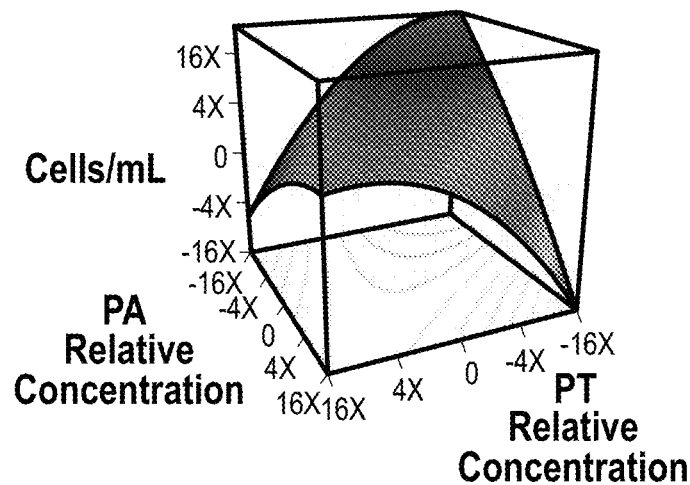
FIG. 8A
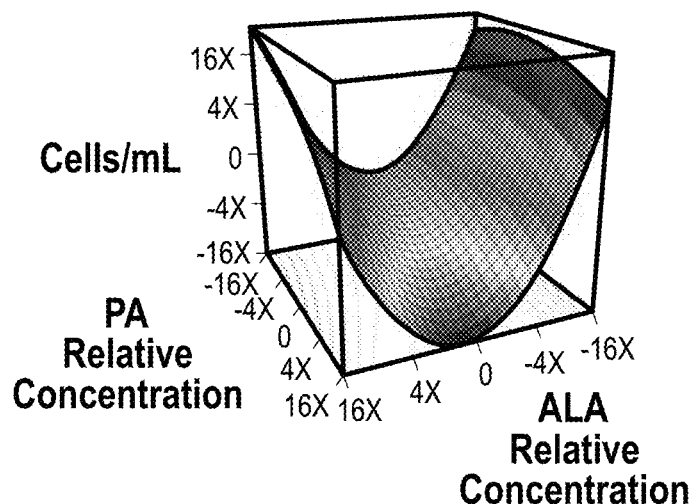
FIG. 8B

CHEMICALLY DEFINED SERUM REPLACEMENTS FOR CELL CULTURE

CROSS-REFERENCE TO RELATED APPLICATION

This application claims the benefit of U.S. Provisional Application No. 63/228,328 filed Aug. 2, 2021 the disclosure of which is hereby incorporated by reference in its entirety.

BACKGROUND

1. Field

The present invention relates to the replacement of serum and animal product containing supplements for ex vivo culture of cells with chemically defined animal-derived component free supplements specifically formulated for each cell type as provided herein

2. Discussion of Related Art

Use of sera and serum albumins has always been a "black box" approach to human and animal cell culture supplementation, providing a variety of fats, nutrients, hormones and biologically active molecules in unknown and variable amounts. Variability of sera by batch has been a recognized problem for decades (Yuta, A. (2017) *Animal-cell culture media: History, characteristics, and current issues* Reproductive medicine and biology 16(2), p.99-117; Omole, A. (2018). *Ten years of progress and promise of induced pluripotent stem cells: historical origins, characteristics, mechanisms, limitations, and potential applications. Peerj* 6: 47) and its deleterious effect on research results has long been noted (Wei, Z., (2016) *Fetal Bovine Serum RNA Interferes with the Cell Culture derived Extracellular RNA* Scientific Reports 6, Article number: 31175; Yao T, (2017) *Animal-cell culture media: History, characteristics, and current issues.* Reproductive Medicine and Biology 16(2): 99-117), but recently it has been discovered that both serum and serum albumin can carry toxins (Gstraunthaler, G. (2013). *A plea to reduce or replace fetal bovine serum in cell culture media.* Cytotechnology, 65(5), 791-793), drugs and prions (Yao T, (2017) *Animal-cell culture media: History, characteristics, and current issues.* Reproductive Medicine and Biology 16(2):99-117), and viral particles (Erickson GA, (1991) *Viral contamination of fetal bovine serum used for tissue culture: risks and concerns* Developments in Biological Standardization 75 p173-175), which can contaminate entire cell lines. Testing to ensure these contaminants are not passed to users of resulting cells and cell-based products is expensive at best. At worst, as in the case of prion contamination, there is no reliable test. This makes continued use of sera and serum albumins highly problematic for culture of cells used in applications intended for human use.

The albumin protein, commonly used in "serum free" supplements and media, has the capacity to carry many different compounds, including drugs, toxins, prions and other contaminants, and is highly variable in its binding behaviors and native cargoes (Fasano, M., (2005). *The extraordinary ligand binding properties of human serum albumin. IUBMB Life* 57(12): 787-796). Albumin binding affinities are affected allosterically by numerous molecules. When cargo is delivered, binding affinities of other sites are affected, leaving empty sites available to bind to nutrients in solution (Lexa KW, (2014) A Structure-Based Model for Predicting Serum Albumin Binding. PLoS ONE 9(4): e93323). This makes serum albumin a major contributor to variability due to its cargo and its tendency to stochastically sequester nutrients in media, thereby altering their availability.

In general, cells respond to the extracellular environment through processes such as protein or hormone signaling, epigenetic remodeling, and signal response cascades, to name a few. The extracellular environment can be beneficial or harmful depending on the specific needs of the cell type in question. Cellular response to sera includes epigenetic remodeling, which can significantly affect the delicate signaling and cloning protocols currently being developed to produce cell therapies and products (Lee, S. M. (2010). Activation and repression of cellular immediate early genes by serum response factor cofactors. *The Journal of biological chemistry*, 285(29), 22036-22049). Serum responses vary widely concomitant to cell type and culture conditions, generating metabolic and phenotypical changes (Nielsen, W. J. (2018). *Comparative Serum Challenges Show Divergent Patterns of Gene Expression and Open Chromatin in Human and Chimpanzee.* Genome Biology and Evolution.,10(3), 826-839) leading to the variability of research results long associated with serum use (. Yuta, A. (2017) *Animal-cell culture media: History, characteristics, and current issues* Reproductive medicine and biology 16(2), p.99-117; Gstraunthaler, G. (2013). *A plea to reduce or replace fetal bovine serum in cell culture media.* Cytotechnology, 65(5), 791-793).

Levels and types of nutrients and contaminants in serum vary widely (Rauch, C. (2011) Alternatives to the *Use of Fetal Bovine Serum: Human Platelet Lysates as a Serum Substitute in Cell Culture Media.* Altex-Alternatives to Animal Experimentation 28(4): 305-316) and a complete inventory of components of any single batch would be difficult and expensive to obtain. When sera are used in cell culture media, this wide range of unknowns can interact with cells, causing unintended variability in experimental results by causing epigenetic (Lee, S. M.. (2010). Activation and repression of cellular immediate early genes by serum response factor cofactors. *The Journal of biological chemistry*, 285(29), 22036-22049; Newman, A. M. (2010). *Lab-Specific Gene Expression Signatures in Pluripotent Stem Cells.* Cell Stem Cell 7(2): 258-262), metabolic (Desai, N., P. Rambhia (2015). *Human embryonic stem cell cultivation: historical perspective and evolution of xeno-free culture systems.* Reproductive Biology and Endocrinology 1) and phenotypic (Arodin Selenius L. *The Cell Culture Medium Affects Growth, Phenotype Expression and the Response to Selenium Cytotoxicity in A549 and HepG2 Cells. Antioxidants* (Basel). 2019;8(5):130) changes and potentially causing damaging contamination. Contamination renders entire cell populations, and products of those cells, unsafe for therapeutic use or human consumption. It is difficult and expensive to positively validate that cultured cells and cell products are free of contamination once they have been exposed. Methods and costs for these validations are among the most significant obstacles to forward progress of advanced cell applications (Gstraunthaler, G., (2013). *A plea to reduce or replace fetal bovine serum in cell culture media.* Cytotechnology, 65(5), 791-793; Yao T, Asayama Y. (2017) *Animal- cell culture media: History, characteristics, and current issues.* Reproductive Medicine and Biology 16(2): 99-117; Yao T, Asayama Y. (2017) *Animal-cell culture media: History, characteristics, and current issues. Reproductive Medicine and Biology* 16(2):99-117; Nielsen O. (1995) Changing sera mind-set. Nature Biotechnology.

13:626). Once contamination has potentially occurred, there is no known way to reliably determine or mitigate the effects of that contamination on cell viability and phenotype.

New animal-free compositions that may be used to culture cells are needed.

SUMMARY

The present disclosure is based, at least in part, on the discovery and development of a line of cell type specific, chemically defined animal derived product free media supplements that completely replace serum in cell culture media to achieve optimal culturing conditions for a variety of cell types.

In various aspects, a chemically defined media supplement is provided comprising: (a) ascorbyl palmitate, docosahexanoic acid and cholesterol sulfate; or (b) ITSE (Insulin, transferrin, selenium, ethanolamine), Trace Elements A, alpha linolenic acid, fibroblast growth factor, insulin-like growth factor, and at least two components selected from the group consisting of docosahexanoic acid, oleic acid, cholesterol sulfate, palmitoleic acid; ascorbyl palmitate, vitamin D3, and valproic acid; wherein the chemically defined media supplement is animal derived product free.

In various aspects, the chemically defined media supplement comprises (a). In various aspects, the chemically defined media supplement of (a) further comprises palmitoleic acid, ascorbic acid, silver, vitamin A, vitamin D3, vitamin K, or a combination of any two or more thereof. In various aspects, the chemically defined media supplement of (a) further comprises oleic acid, alpha linoleic acid or both oleic acid and alpha linoleic acid.

In still other aspects, the chemically defined media supplement of claim 1, comprising (b) In some instances, the chemically defined media supplement of (b) comprises ITSE (Insulin, transferrin, selenium, ethanolamine), Trace Elements A, alpha linolenic acid, fibroblast growth factor, insulin-like growth factor, oleic acid, docosahexanoic acid, and vitamin D3. In various aspects, the chemically defined media supplement of (b) further comprises epithelial growth factor (EGF), vitamin D3, palmitoleic acid, ascorbyl palmitate, cholesterol, silver, vitamin A, vitamin D3, vitamin K, N-acetyl cysteine, retinoic acid or a combination of any of two or more thereof. In still other aspects, the chemically defined media supplement of (b) further comprises hydrocortisone.

In various aspects, the chemically defined media supplement of (b) comprises ITSE (Insulin, transferrin, selenium, ethanolamine), Trace Elements A, alpha linolenic acid, fibroblast growth factor, insulin-like growth factor (IGF) cholesterol sulfate and palmitoleic acid. In some aspects, the chemically defined media supplement of (b) further comprises epithelial growth factor (EGF), Vitamin D3, ascorbyl palmitate, oleic acid, valproic acid, caprylic acid, hydrocortisone, vitamin A, vitamin D3, vitamin K, or a combination of any two or more thereof. In some aspects, the chemically defined media supplement of (b) further comprises hydrocortisone, hypoxanthine/thymidine, retinoic acid, beta-hydroxy butyrate, poloxamer-188 or a combination of any two or more thereof.

In various aspects, the chemically defined media supplement of (b) comprises ITSE (Insulin, transferrin, selenium, ethanolamine), Trace Elements A, alpha linolenic acid, fibroblast growth factor, insulin-like growth factor, cholesterol sulfate, palmitoleic acid, ascorbyl palmitate, and valproic acid. In some aspects, the chemically defined media supplement of (b) further comprises epithelial growth factor (EGF), vitamin D3, docosahexanoic acid, oleic acid, N-acetyl cysteine, silver, vitamin A, vitamin K, retinoic acid or a combination of any two or more thereof. In various aspects, the chemically defined media supplement of (b) may further comprise hydrocortisone.

In various aspects, the chemically defined media supplement comprises (a) ascorbyl palmitate, docosahexanoic acid, cholesterol sulfate, palmitoleic acid, ascorbic acid, silver, vitamin A, vitamin D3, vitamin K, oleic acid and alpha linolenic acid; or (b) ITSE (insulin, transferrin, selenium, ethanolamine), Trace Elements A, alpha linolenic acid, docosahexanoic acid, oleic acid, FGF (fibroblast growth factor), IGF (insulin-like growth factor), vitamin D3, EGF (epithelial growth factor), palmitoleic acid, ascorbyl palmitate, cholesterol sulfate, silver, vitamin A, vitamin K, N-acetyl cysteine, retinoic acid and hydrocortisone; or (c) ITSE (insulin, transferrin, selenium, ethanolamine), Trace Elements A, FGF (fibroblast growth factor), IGF (insulin-like growth factor), cholesterol sulfate, alpha linolenic acid, palmitoleic acid, EGF (epithelial growth factor), vitamin D3, ascorbyl palmitate, oleic acid, valproic acid, caprylic acid, hydrocortisone, silver, vitamin A, vitamin K, thiazovivin, hypoxanthine/thymidine, hydrocortisone, retinoic acid, beta-hydroxy butyrate, and poloxamer-188; or (d) ITSE (insulin, transferrin, selenium, ethanolamine), Trace Elements A, FGF (fibroblast growth factor), IGF (insulin-like growth factor, cholesterol sulfate, an alpha linolenic acid, palmitoleic acid, ascorbyl palmitate, valproic acid, EGF (epithelial growth factor), vitamin D3, docosahexanoic acid, oleic acid, N-acetyl cysteine, silver, vitamin A, vitamin K, retinoic acid, and hydrocortisone.

In any of the above or related aspects of the present disclosure, the chemically defined media supplement does not comprise albumin.

In further aspects, the chemically defined media supplement may be used to supplement a culture media for induced pluripotent stem cells (iPSCs), human foreskin fibroblasts (HFF), human embryonic kidney (HEK) cells, or smooth muscle cells (SMCs).

In further aspects of the present disclosure, a method of culturing a cell is provided, the method comprising adding to a cell culture medium a chemically defined media supplement of described herein and culturing the cell in the cell culture medium. In various aspects, the cell is an induced pluripotent stem cell, and the chemically defined media supplement comprises ascorbyl palmitate, docosahexanoic acid and cholesterol sulfate. In other aspects, the cell is a human foreskin fibroblast (HFF), and the chemically defined media supplement comprises ITSE (Insulin, transferrin, selenium, ethanolamine), Trace Elements A, Alpha Linolenic Acid, fibroblast growth factor, insulin-like growth factor, oleic acid, Vitamin D3, and docosahexanoic acid. In still other aspects, the cell is a human embryonic kidney (HEK) cell, and the chemically defined media supplement comprises ITSE (Insulin, transferrin, selenium, ethanolamine), Trace Elements A, alpha linolenic acid, fibroblast growth factor (FGF), insulin-like growth factor (IGF) cholesterol sulfate and palmitoleic acid. In still other aspects, the cell is a smooth muscle cell (SMC) and the chemically defined media supplement comprises ITSE (Insulin, transferrin, selenium, ethanolamine), Trace Elements A, alpha linolenic acid, fibroblast growth factor, insulin-like growth factor, cholesterol sulfate, palmitoleic acid, ascorbyl palmitate, and valproic acid.

BRIEF DESCRIPTION OF THE DRAWINGS

The following drawings form part of the present specification and are included to further demonstrate certain aspects of the present disclosure, which can be better understood by reference to the drawing in combination with the detailed description of specific embodiments presented herein.

FIG. 7 shows the result of a spectrophotometric assay using phenolphthalein indicator to determine the complexation of efficiency of 5 lipids complexed with cyclodextrins.

FIGS. 8A & 8B shows Design of Experiments data showing two-factor interaction results on HFF cells. Vertical axes reflect cell numbers/mL after culture for 5 days. Horizontal axes correspond to increasing concentration of indicated lipids. Result A (FIG. 8A) shows agonistic relationship between PA (palmitoleic acid) and PT (palmitate), while result B (FIG. 8B) shows antagonist relationship between PA and α linolenic acid (ALA). Repeated optimizations support development of highly effective cell-specific supplements.

DETAILED DESCRIPTION

Figure 1:
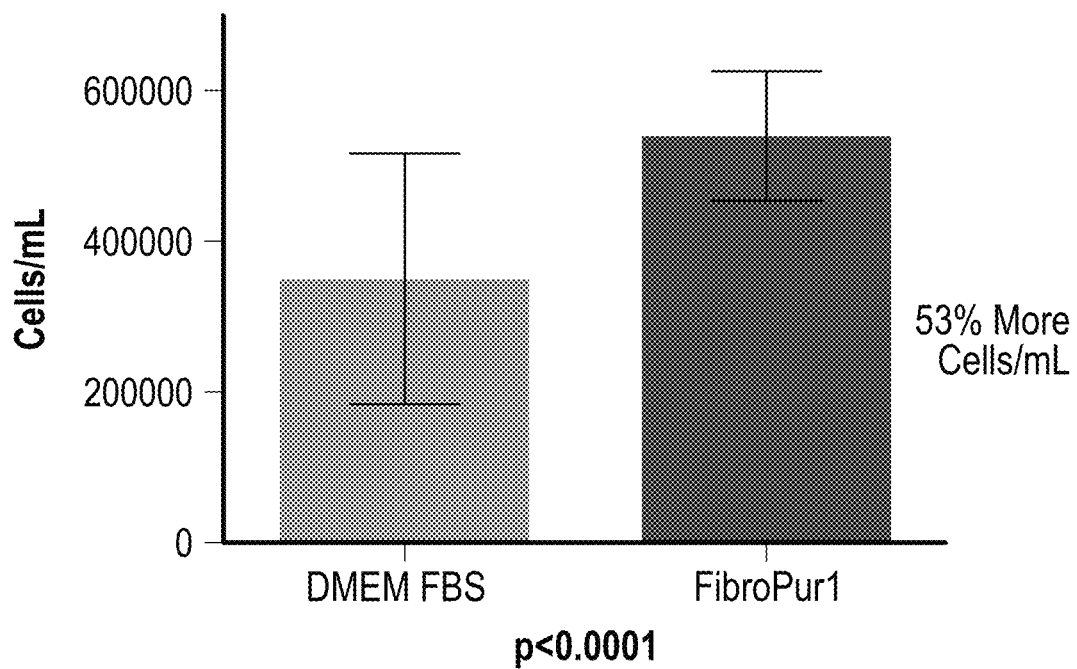
FIG. 1 shows proliferation and standard deviation of HFF cells grown in DMEM medium supplemented with optimized chemically defined supplement, compared to supplementation with FBS. Counted day 10.

The following detailed description references the accompanying drawings that illustrate various embodiments of the present inventive concept. The drawings and description are intended to describe aspects and embodiments of the present inventive concept in sufficient detail to enable those skilled in the art to practice the present inventive concept. Other components can be utilized, and changes can be made without departing from the scope of the present inventive concept. The following description is, therefore, not to be taken in a limiting sense. The scope of the present inventive concept is defined only by the appended claims, along with the full scope of equivalents to which such claims are entitled.

I. Terminology

The phraseology and terminology employed herein are for the purpose of description and should not be regarded as limiting. For example, the use of a singular term, such as, "a" is not intended as limiting of the number of items. Also, the use of relational terms such as, but not limited to, "top," "bottom," "left," "right," "upper," "lower," "down," "up," and "side," are used in the description for clarity in specific reference to the figures and are not intended to limit the scope of the present inventive concept or the appended claims.

Further, as the present inventive concept is susceptible to embodiments of many different forms, it is intended that the present disclosure be considered as an example of the principles of the present inventive concept and not intended to limit the present inventive concept to the specific embodiments shown and described. Any one of the features of the present inventive concept may be used separately or in combination with any other feature. References to the terms "embodiment," "embodiments," and/or the like in the description mean that the feature and/or features being referred to are included in, at least, one aspect of the description. Separate references to the terms "embodiment," "embodiments," and/or the like in the description do not necessarily refer to the same embodiment and are also not mutually exclusive unless so stated and/or except as will be readily apparent to those skilled in the art from the description. For example, a feature, structure, process, step, action, or the like described in one embodiment may also be included in other embodiments but is not necessarily included. Thus, the present inventive concept may include a variety of combinations and/or integrations of the embodiments described herein. Additionally, all aspects of the present disclosure, as described herein, are not essential for its practice. Likewise, other systems, methods, features, and advantages of the present inventive concept will be, or become, apparent to one with skill in the art upon examination of the figures and the description. It is intended that all such additional systems, methods, features, and advantages be included within this description, be within the scope of the present inventive concept, and be encompassed by the claims.

As used herein, the term "about," can mean relative to the recited value, e.g., amount, dose, temperature, time, percentage, etc., ±10%, ±9%, ±8%, ±7%, ±6%, ±5%, ±4%, ±3%, ±2%, or ±1%.

The terms "comprising," "including," "encompassing" and "having" are used interchangeably in this disclosure. The terms "comprising," "including," "encompassing" and "having" mean to include, but not necessarily be limited to the things so described.

The terms "or" and "and/or," as used herein, are to be interpreted as inclusive or meaning any one or any combination. Therefore, "A, B or C" or "A, B and/or C" mean any of the following: "A," "B" or "C"; "A and B"; "A and C"; "B and C"; "A, B and C." An exception to this definition will occur only when a combination of elements, functions, steps or acts are in some way inherently mutually exclusive.

As used herein, the terms "chemically defined" can refer to a composition whose components are specifically known. As used herein, "animal derived" means produced from or by an animal. For example, serum is "animal derived". Albumin, a component obtained from serum, is also "animal derived". As used herein "animal derived product free" means that the composition is free from any product produced from or by an animal. For example, a typical "animal derived product" used in cell culture media is serum or albumin. Serum is an example of an animal derived product that is also not chemically defined, as it is impossible to precisely identify each and every component within it.

Albumin is an animal derived component that could be chemically defined (e.g., added to a composition at a precise concentration), but is not used in the compositions herein. Therefore, as understood herein, a composition may be chemically defined and comprise only components that may be precisely identified and quantified. At the same time, a composition may be "animal derived product free" and contain no components that are derived from animals. The compositions herein are advantageously both chemically defined and animal-derived product free. Accordingly, the compositions herein do not comprise any product derived from an animal. In some aspects, the compositions do not comprise albumin. In other aspects, the compositions do not comprise serum. It is also understood that "chemically defined" is not necessarily synonymous with "consisting of". In other words, a "chemically defined" composition may comprise ingredients not defined or listed herein, as long as those ingredients are known to the manufacturer of the composition and clearly quantifiable using standard assays in the art.

It should also be understood that, unless clearly indicated to the contrary, in any methods claimed herein that include more than one step or act, the order of the steps or acts of the method is not necessarily limited to the order in which the steps or acts of the method are recited.

II. Chemically Defined Media Supplements

The present disclosure provides for various chemically defined media supplements that may be added to a suitable cell media to improve or enhance cell health, growth, maturity and/or proliferation in the media. Importantly, each chemically defined media supplement comprises no animal derived components and guarantees that the chemically defined media supplement does not add any possible contaminants to the cell media or the cells therein.

The present invention provides chemically defined media supplements for basal media, based on the needs of each cell type, comprising or obtained by one or more ingredients selected from the group consisting of one or more carrier vehicles (Table 1), one or more lipid moieties (Table 2), trace elements, one or more insulin or insulin substitutes, one or more transferrins or transferrin substitutes, one or more hydrophobic vitamins, one or more bioactive molecules, one or more antioxidants and/or one or more growth factors or growth factor substitutes wherein a basal cell culture medium supplemented with the supplements is capable of supporting the expansion of different cell types including but not limited to Fibroblasts, human embryonic kidney cells (HEK), induced pluripotent stem cells (iPSC), Lung cells (e.g., WI-38), adipose cells, and smooth muscle cells in chemically defined conditions.

In various aspects, suitable chemically defined media supplements provided herein may comprise suitable carrier vehicles or ligands. Suitable carrier vehicles and ligands that may be used are provided in Table 1 below.

TABLE 1

Carrier Vehicles and Ligands Used in Chemically Defined Media Supplement

| Carrier Name | Abbreviation |
|---|---|
| alpha cyclodextrin | ACD |
| ascorbic acid | ASC |
| Beta cyclodextrin | BCD |
| gamma cyclodextrin | GCD |

TABLE 1-continued

Carrier Vehicles and Ligands Used in Chemically Defined Media Supplement

| Carrier Name | Abbreviation |
|---|---|
| heptakis (2,6-di-O-methyl) beta cyclodextrin | HOBCD |
| hydroxypropyl beta cyclodextrin | HPBCD |
| methyl beta cyclodextrin | MBCD |
| N-acetyl cysteine | NAC |
| retinoic acid | RA |
| silver nanoparticles | CAG |
| Sodium butyrate | NaBut |
| sulfobuty ether sodium cyclodextrin | SBECD |

In various aspects, suitable chemically defined media supplements provided herein may comprise one or more lipid moieties (Table 2). In various embodiments, the chemically defined media supplements comprise one or more omega 3 fatty acids (e.g., alpha linolenic acid, stearidonic acid, docosapentanoic acid, docosahexanoic acid, eicosapentanoic acid, or hexadecatrienoic acid).

TABLE 2

Lipids Used in Chemically Defined Media Supplements

| Lipid number | Lipid Name | Saturation* |
|---|---|---|
| 4:0 | Butyric acid | Un |
| 8:0 | Caprylic acid | Un |
| 10:0 | Capric acid | Un |
| 12:0 | Lauric acid | Un |
| 14:0 | Myristic acid | Un |
| 16:0 | Palmitic acid | Un |
| 16:1 | Palmitoleic acid | mono ω7 |
| 16:3 | Hexadecatrienoic acid | poly ω3 |
| 18:0 | Stearic acid | Un |
| 18:1 | Oleic acid | mono ω9 |
| 18:2 | Linolenate acid | poly ω6 |
| 18:3 | Alpha linolenic acid | poly ω3 |
| 18:4 | Stearidonic acid | poly ω3 |
| 20:0 | Arachidic acid | Un |
| 20:1 | Eicosenoic acid | mono ω9 |
| 20:1 | Sphingosine | mono ω16 |
| 20:4 | Eicosatrienoic acid | poly ω3 |
| 20:4 | Arachidonic acid | poly ω6 |
| 20:5 | Eicosapentanoic acid | poly ω3 |
| 22:1 | Erucic acid | mono ω9 |
| 22:5 | Docosapentanoic acid | poly ω3 |
| 22:6 | Docosahexanoic acid | poly ω3 |
| NA | Cholesterol | NA |
| NA | Cholesterol α-linolenate | NA |
| NA | Cholesterol sulfate | NA |
| NA | 25 hydroxy cholesterol | NA |
| NA | 20{S}-hydroxycholesterol | NA |
| NA | Fucosterol | NA |
| NA | 7-keto Cholesterol | NA |
| NA | cholesteryl palmitate | NA |
| NA | Cholesteryl Palmitoleate | NA |
| NA | 3B-hydroxy-5 cholestenoic acid | NA |

*ω = omega

In various aspects, the chemically defined media supplements may comprise trace elements, e.g., one or more of Cupric Sulfate, Ferric Citrate, Sodium Selenite, and Zinc Sulfate. In various aspects, these trace elements may be provided or added to chemically defined media supplements from commercially available concentrated solutions (e.g., Trace Elements A from Corning). Suitable trace element solutions that may be incorporated into the chemically defined media supplements are provided in the table below.

| Trace Element Product | Components | Product Number | Stock Concentration | Concentration in Chemically Defined Media Supplements |
|---|---|---|---|---|
| Trace Elements A | Cupric Sulfate, Ferric Citrate, Sodium Selenite, and Zinc Sulfate | Corning® 25-021-CI | 1000× | 100× |

The composition of Trace Elements A provided in the previous Table is chemically defined and available to one of ordinary skill in the art. For ease of reference, the chemical make-up of commercially available Trace Elements supplements that may be used in the present invention are provided in the Table below. Each Trace Element Supplement (commercially available as provided in the previous Table) is provided at a 1000×concentration. Accordingly, in various aspects, the chemically defined media supplements herein comprise each component in the Trace Elements (Trace Elements A) at a 10×-500×concentration, where 1× is understood to be an optimized concentration for a cell culture media. In some aspects, the chemically defined media supplements herein comprise 10×-500×, 10×-400×, 10×-300×, 10×-250×, 10×-200×, 10×-100×, or 10×-50× Trace Elements A. In various aspects, the chemically defined media supplements comprise 10×, 50×, 100×, or 1000× Trace Elements A. In various aspects, the chemically defined media supplement comprises 100× Trace Elements A.

| Component | Trace Elements A (1000×) [mg/L] |
|---|---|
| $CuSO_4 \cdot 5H_2O$ | 1.60 |
| $ZnSO_4 \cdot 7H_2O$ | 863.00 |
| Selenite · 2Na | 17.30 |
| Ferris citrate | 1155.10 |

In other aspects, the chemically defined media supplements for basal media may comprise one or more insulin or insulin substitutes, one or more transferrins or transferrin substitutes, one or more hydrophobic vitamins, one or more bioactive molecules, one or more antioxidants and/or one or more growth factors or growth factor substitutes wherein a basal cell culture medium supplemented with the supplements is capable of supporting the expansion of different cell types including but not limited to Fibroblasts, human embryonic kidney cells (HEK), induced pluripotent stem cells (iPSC), Lung cells (e.g., WI-38), adipose cells and smooth muscle cells in chemically defined conditions.

In various aspects, the chemically defined media supplements comprise Insulin-Transferrin-Selenium-Ethanolamine (ITSE). ITSE is a stock solution containing defined concentrations of insulin, transferrin, selenium, and ethanolamine in a salt solution (e.g., Earle's balanced salt solution). As shown in the Table below, exemplary commercially available ITSE supplements is sold at a 100× concentration (comprising 1 g/L insulin, 0.55 g/L Transferrin, 0.00067 g/L Sodium Selenite and 0.20 g/L Ethanolamine in an Earle's balanced salt solution comprising 2.2 g/L $NaHCO_3$ and 1 g/L glucose). In various aspects, chemically defined media supplement also contain ITSE components at 100× concentration (i.e., the ITSE solution is not further diluted in making the chemically defined media supplement). In some aspects, this means the ITSE stock solution is a base solution used in preparing the chemically defined media supplements herein.

| ITSE Stock Solution (100×) Concentrations (g/L) | | | | | |
|---|---|---|---|---|---|
| Insulin | Transferrin | Sodium Selenite | Ethanolamine | NaHCO3* | Glucose* |
| 1 | 0.55 | 0.00067 | 0.20 | 2.2 g/L | 1 |

*Component of Earle's balanced salt solution used as solvent/buffer.

The present invention also provides chemically defined media supplements comprising or obtained by combining one or more nutrients selected from the group consisting of N-acetyl-L cysteine, ethanolamine, hydrocortisone, 2-mercaptoethanol, sodium butyrate, CoQ10, silver colloid, retinoic acid, phosphatidylcholine, sphingomyelin, glycerophosphocholine, phosphocholine, vitamins A, E and K, insulin, transferrin, selenium, thiazovivin, vitronectin, fibronectin, and growth factors or growth factor substitutes. Provided are compositions and methods for culturing and/or expanding specific cell types (e.g., fibroblasts, smooth muscle cells) where the cells may produce one or more products (e.g., one or more protein (e.g., one or more heterologous protein), one or more nucleic acid molecule (e.g., one or more heterologous protein), or be used for therapeutic applications (e.g. stem cell transplantation). Further provided herein are, inter alia, compositions, systems, and methods for culturing and/or expanding cells (e.g., HEK cells), as well as specific methods for passaging, freezing, and thawing different cell types.

In an aspect, a chemically defined culture supplement composition (e.g. a chemically defined cell culture supplement composition) comprising a cyclodextrin and at least one lipid, trace elements, non-animal derived growth factors, and other bioactive molecules necessary to support robust cell health and proliferation is included herein. In some embodiments, the composition comprises alpha linolenic acid, at least one other omega-3 fatty acid, oleic acid, caprylic acid, palmitic acid, cholesterol, growth factors specific to cell type, and a cyclodextrin.

In many instances, the cyclodextrin is a methylated cyclodextrin. In many instances, cyclodextrin or methylated cyclodextrin is present at a level from about 10 μM to about 100 μM. In many instances, the cholesterol is a synthetic cholesterol, and the cholesterol is present at a concentration of from about 100 nM to about 30 μM. In some instances, the polyunsaturated fatty acid is one or more fatty acids selected from the group consisting of, alpha linolenic acid, linolenic acid, oleic acid, palmitic acid, palmitoleic acid, and caprylic acid.

In one aspect, the chemically defined media supplement may comprise at least one component selected from: ascorbyl palmitate, docosahexanoic acid, cholesterol sulfate, ITSE (Insulin, transferrin, selenium, ethanolamine, described above), Trace Elements A (described above), alpha linolenic acid, fibroblast growth factor, insulin-like growth factor, docosahexanoic acid, oleic acid, palmitoleic acid; Vitamin D3 and valproic acid. In various aspects, the chemically defined media supplement may further comprise palmitoleic acid, ascorbic acid, silver, vitamin A, vitamin D3, vitamin K, epithelial growth factor (EGF), ascorbyl palmitate, cholesterol sulfate, silver, N-acetyl cysteine, retinoic acid, oleic acid, valproic acid, caprylic acid, hydrocortisone, docosahexanoic acid, or a combination of any two or more thereof. in still further aspects, the chemically defined media supplement may further comprise hydrocortisone, hypoxanthine/thymidine, retinoic acid, beta-hydroxy butyrate, poloxamer-188 (e.g., PLURONIC™ F-68), and/or thiazovivin.

In various aspects, the chemically defined media supplements may comprise (a) Ascorbyl palmitate, docosahexanoic acid and cholesterol sulfate; or (b) ITSE (Insulin, transferrin, selenium, ethanolamine), Trace Elements A, alpha linolenic acid, fibroblast growth factor, insulin-like growth factor, and at least two components selected from the group consisting of docosahexanoic acid, oleic acid, cholesterol sulfate, palmitoleic acid; ascorbyl palmitate, Vitamin D3 and valproic acid.

For example, in some aspects the chemically defined media supplements may comprise ascorbyl palmitate, docosahexanoic acid and cholesterol sulfate. In various aspects, the chemically defined media supplements may comprise ITSE (Insulin, transferrin, selenium, ethanolamine), Trace Elements A, alpha linolenic acid, fibroblast growth factor, insulin-like growth factor, oleic acid and, docosahexanoic acid, and Vitamin D3. In another aspect, the chemically defined media supplements may comprise ITSE (Insulin, transferrin, selenium, ethanolamine), Trace Elements A, alpha Linolenic Acid, fibroblast growth factor, insulin-like growth factor (IGF) cholesterol sulfate and palmitoleic acid. In still other aspects, the chemically defined media supplements may comprise ITSE (Insulin, transferrin, selenium, ethanolamine), Trace Elements A, alpha linolenic acid, fibroblast growth factor, insulin-like growth factor, cholesterol sulfate, palmitoleic acid, ascorbyl palmitate, and valproic acid.

In further aspects, the chemically defined media supplements may comprise or further comprise one or more components from Table A, below. Also shown in Table A are exemplary chemically defined media supplements for certain cell types (e.g., IPSCs, HFFs, HEK, or SMCs).

TABLE A

Preferred Components in Chemically Defined Media Supplements

| Component | IPSC | HFF | HEK | SMC |
|---|---|---|---|---|
| ascorbyl palmitate | X | | | X |
| docosahexanoic acid | X | X | | |
| cholesterol sulfate | X | | X | X |
| ITSE (Insulin, transferrin, selenium, ethanolamine) | | X | X | X |
| Trace Elements A | | X | X | X |
| alpha linolenic acid | | X | X | X |
| fibroblast growth factor (FGF) | | X | X | X |
| insulin-like growth factor (IGF) | | X | | X |
| oleic acid | X | | | |
| palmitoleic acid | | | X | X |
| Vitamin D3 | X | | | |
| valproic acid | | | | X |

IPSC = Induced Pluripotent Stem Cells,
HFF = Human foreskin fibroblasts,
HEK = Human embryonic kidney cells,
SMC = smooth muscle cells.

Any of the previously described chemically defined media supplements may further comprise one or more of palmitoleic acid, ascorbic acid, silver, vitamin A, vitamin D3, vitamin K, epithelial growth factor (EGF), ascorbyl palmitate, cholesterol, N-acetyl cysteine, retinoic acid, oleic acid, valproic acid, caprylic acid, hydrocortisone and/or docosahexanoic acid. Suitable additional components that may be added to any of the previously described supplements (e.g., as exemplified in Table A) are shown in Table B, along with illustrative supplement combinations for certain cell types.

TABLE B

Secondary Components in Chemically Defined Media Supplements

| Component | IPSC | HFF | HEK | SMC |
|---|---|---|---|---|
| palmitoleic acid | X | X | | |
| ascorbic acid | X | | | |
| silver | X | X | | X |
| vitamin A | X | X | X | X |
| vitamin D3 | X | X | X | X |
| vitamin K | X | X | X | X |
| epithelial growth factor (EGF) | | X | X | X |
| ascorbyl palmitate | | X | X | |
| cholesterol | | X | | |
| N-acetyl cysteine | | X | | X |
| retinoic acid | | X | | X |
| oleic acid | | X | | X |
| valproic acid | | | X | |
| caprylic acid | | | X | |
| hydrocortisone | | | X | |
| docosahexanoic acid | | | | X |

IPSC = Induced Pluripotent Stem Cells,
HFF = Human foreskin fibroblasts,
HEK = Human embryonic kidney cells,
SMC = smooth muscle cells.

Any of the previously described chemically defined media supplements may further comprise one or more of oleic acid, alpha linoleic acid, hydrocortisone, hypoxanthine/thymidine, retinoic acid, beta-hydroxy butyrate, thiazovivin, and/or poloxamer-188 (e.g., PLURONIC™ F-68). Exemplary combinations of these additional components that may be used in the chemically defined media supplements provided herein are shown in Table C.

TABLE C

Tertiary Components in Chemically Defined Media Supplements

| Component | IPSC | HFF | HEK | SMC |
|---|---|---|---|---|
| oleic acid | X | | | |
| alpha linoleic acid | X | | | |
| hydrocortisone | | X | X | X |
| hypoxanthine/thymidine | | | X | |
| retinoic acid | | | X | |
| beta-hydroxy butyrate | | | X | |
| poloxamer-188 | | | X | |
| thiazovivin | | | X | |

IPSC = Induced Pluripotent Stem Cells,
HFF = Human foreskin fibroblasts,
HEK = Human embryonic kidney cells,
SMC = smooth muscle cells.

Accordingly, in various aspects, suitable combinations of the components described above that may be used in illustrative chemically defined media supplements are provided in Table D. In Table D, components categorized as "a" are considered more important to the media composition, "b" are less important, and "c" are least important. Any combinations of the following components may be envisioned to prepare tailored chemically defined media supplements for these or other cell types.

TABLE D

Illustrative Chemically Defined Media Supplements

| Component | IPSC | HFF | HEK | SMC |
|---|---|---|---|---|
| ascorbyl palmitate | a | b | b | a |
| docosahexanoic acid | a | a | | b |
| cholesterol sulfate | a | b | a | a |
| ITSE (Insulin, transferrin, selenium, ethanolamine) | | a | a | a |
| Trace Elements A | | a | a | a |
| alpha linolenic acid | c | a | a | a |
| fibroblast growth factor (FGF) | | a | a | a |
| insulin-like growth factor (IGF) | | a | | a |
| oleic acid | c | a | b | b |
| palmitoleic acid | b | b | a | a |
| vitamin D3 | b | a | b | b |
| valproic acid | | | b | a |
| ascorbic acid | b | | | |
| silver | b | b | | b |
| vitamin A | b | b | b | b |
| vitamin K | b | b | b | b |
| epithelial growth factor (EGF) | | b | b | b |
| N-acetyl cysteine | b | | | b |
| retinoic acid | b | | c | b |
| caprylic acid | | | b | |
| hydrocortisone | c | b/c | | c |
| hypoxanthine/thymidine | | | c | |
| beta-hydroxy butyrate | | | c | |
| poloxamer-188 | | | c | |
| thiazovivin | | | b | |

IPSC = Induced Pluripotent Stem Cells,
HFF = Human foreskin fibroblasts,
HEK = Human embryonic kidney cells,
SMC = smooth muscle cells.

In general, the chemically defined media supplements described herein may be provided as a concentrated formulation, which may be diluted into a suitable cell culture medium for a given cell type. The supplements provided herein, therefore, may be provided at a concentration 10×, 100×, or 1000× of a target concentration in the media. The supplements may be formulated at a concentration 10×-200× of a target concentration in the media. The supplements may be formulated at a 10×, 20×, 30×, 40×, 50×, 60×, 70×, 80×, 90×, 100×, 200×, 300×, 400×, 500×, 600×, 700×, 800×, 900×, or 1000× a target concentration in the media. In some aspects, the supplements may be formulated at 100× of a target concentration in the media. In any of these aspects, each of the components in the chemically defined media supplement may be included in the supplement at a concentration 100× that of a target concentration in a cell culture medium. As used herein, "target concentration" means a concentration found to be optimal or appropriate for the component in a cell culture medium. A "target concentration" for a given component may vary depending on the cell type used.

For example, a supplement formulated at 100× strength will comprise each component at a concentration 100× the concentration found to be appropriate or optimal for their inclusion in a cell media for a given cell type. It may be envisioned that a given component may be appropriately or optimally provided at a certain concentration for one cell type and a different concentration for another cell type. Further optimization is possible, e.g., using methods described in the Examples herein. Accordingly, and without being limited to the following, suitable concentrations of various components that may be used in supplements for iPSCs, HFFs, HEKs and SMCs are provided herein in Table E below.

TABLE E

Illustrative Concentrations of Chemically Defined Media Supplement

| Component | Exemplary Concentration Range(s) in Supplement (100×) | Exemplary Concentration Range in Media | IPSC | HFF | HEK | SMC |
|---|---|---|---|---|---|---|
| ascorbyl palmitate | 1 mM-1M<br>10 μM-1 mM | 1 μM-1 mM<br>10 nM-10 μM | a | b | b | a |
| docosahexanoic acid | 1 μM-10 mM | 1 nM-10 μM | a | a | | b |
| cholesterol sulfate | 10 μM-10 mM | 10 nM-10 μM | a | b | a | a |
| ITSE (Insulin, transferrin, selenium, ethanolamine) | 100× | 1× | | a | a | a |
| Trace Elements A | 100× | 1× | | a | a | a |
| Alpha Linolenic Acid | 1 mM-10 mM | 10 nM-10 μM | c | a | a | a |
| fibroblast growth factor | 1-5 μg/mL | 5-100 ng/mL | | a | a | a |
| insulin-like growth factor | 1-500 μg/mL | 5-100 ng/mL | | a | | a |
| oleic acid | 1 mM-100 mM | 1 nM-10 mM | c | a | b | b |
| palmitoleic acid | 1 mM-10 mM | 100 nM-10 μM | b | b | a | a |
| Vitamin D3 | 1 μM-1 mM | 10 nM-200 nM<br>10 nM-1 μM | b | a | b | b |
| valproic acid; | 10 mM | 100 nM-1 mM | | | b | a |
| ascorbic acid | 1-500 mM | 1 μM-1 mM | b | | | |
| silver | 10,000-32,000 ppm | 100-320 ppm | b | b | | b |
| vitamin A | 100× | 50-200 nM<br>100 nM-5microM | b | b | b | b |
| vitamin K | 100× | 10 nM-1 μM | b | b | b | b |
| epithelial growth factor (EGF) | 1-5 μg/mL | 5-100 ng/mL | | b | b | b |
| N-acetyl cysteine | 100× | 100 nM-10 μM | b | | | b |
| retinoic acid | 50 μM-1 mM | 10 nM-500 nM<br>100 nM-100 μM | b | | c | b |

TABLE E-continued

Illustrative Concentrations of Chemically Defined Media Supplement

| Component | Exemplary Concentration Range(s) in Supplement (100×) | Exemplary Concentration Range in Media | IPSC | HFF | HEK | SMC |
|---|---|---|---|---|---|---|
| caprylic acid | 10-100 mM | 100 nM-1 mM | | | b | |
| hydrocortisone | 100 μM-1 mM | 1 μM-20 μM | | c | b/c | c |
| hypoxanthine/thymidine | 100× | Standard Conc. | | | c | |
| beta-hydroxy butyrate | 10-100 mM | 100 nM-1 mM | | | c | |
| polyoxamic-188 | 100× | 0.5-5 g/L | | | c | |
| thiazovivin | 100× | 10 nM-500 nM | | | b | |

As an illustrative example, a chemically defined media supplement for induced pluripotent stem cells is provided, wherein the supplement may be added to a suitable cell growth medium and adds 1 μM-1 mM ascorbyl palmitate, about 1 nM-10 μM docosahexanoic acid and/or about 10 nM-10 μM Cholesterol Sulfate to the medium. In various aspects, the chemically defined media supplement further adds about 100 nM-10 μM Palmitoleic Acid, about 1 μM-1 mM Ascorbic Acid, about 100-320 ppm silver, about 50-200 nM Vitamin A, about 10 nM-200 nM Vitamin D3, and/or about 10 nM-1 μM Vitamin K to the medium. In other aspects, the chemically defined media supplement further adds about 10 nM-10 μM oleic acid and/or about 10 nM-1 μM alpha linolenic acid to the medium.

As an illustrative example, a chemically defined media supplement for induced pluripotent stem cells is provided, wherein the supplement may be added to a suitable cell growth medium and adds about 1 μM-1 mM Ascorbyl Palmitate, about 1 nM-10 μM Docosahexanoic Acid, about 10 nM-10 μM cholesterol sulfate, about 100 nM-10 μM Palmitoleic Acid, about 1 μM-1 mM Ascorbic Acid, about 10 nM-10 μM oleic acid, or about 10 nM-1 μM Alpha Linolenic Acid to the media. In some aspects, the chemically defined media supplement for induced pluripotent stem cells further adds to the medium about 100-320 ppm silver, about 50-200 nM Vitamin A, about 10 nM-200 nM Vitamin D3, and/or about 10 nM-1 μM Vitamin K.

As another illustrative example, a chemically defined media supplement is provided for supplementing a media to culture human foreskin fibroblasts (HFF), wherein the supplement may be added to a suitable cell growth medium and adds a standard concentration of ITSE (insulin, transferrin, selenium, ethanolamine), a standard concentration of Trace Elements A, about 10 nM-10 μM Alpha Linolenic Acid, about 10 nM-10 μM Docosahexanoic Acid, about 1 nM-1 μM oleic acid, about 5-100 ng/mL FGF (Fibroblast Growth Factor), about 5-100 ng/mL IGF (Insulin-like Growth Factor), and/or about 1 nM-1 μM Vitamin D3 to the medium. In various aspects, the chemically defined media supplement further adds about 5-100 ng/mL EGF (Epithelial Growth Factor), about 1 nM-10 μM Palmitoleic Acid, about 10 nM-10 μM Ascorbyl Palmitate, about 10 nM-10 μM Cholesterol Sulfate, about 100-320 ppm silver, about 100 nM-5 μM Vitamin A, about 10 nM-1 μM Vitamin K, about 100 nM-10 microM N-Acetyl Cysteine, and/or about 10 nM-500 nM Retinoic Acid to the medium. In further aspects, the chemically defined media supplement further adds about 1 μM-20 μM hydrocortisone to the medium.

As another illustrative example, a chemically defined media supplement is provided for supplementing a media to culture human foreskin fibroblasts (HFF), wherein the supplement may be added to a suitable cell growth medium and adds a standard concentration of ITSE (insulin, transferrin, selenium, ethanolamine), a standard concentration of Trace Elements A, about 10 nM-10 μM Alpha Linolenic Acid, about 10 nM-10 μM Docosahexanoic Acid, about 1 nM-1 μM oleic acid, about 5-100 ng/mL FGF (Fibroblast Growth Factor), about 5-100 ng/mL IGF (Insulin-like Growth Factor), about 5-100 ng/mL EGF (Epithelial Growth Factor, about 1 nM-1 μM Vitamin D3, about 1 nM-10 μM Palmitoleic Acid, about 10 nM-10 μM Ascorbyl Palmitate, about 10 nM-10 μM Cholesterol Sulfate, and about 1 μM-20 μM Hydrocortisone to the media. In some aspects, the chemically defined media supplement for HFF cells further adds to the media about 100-320 ppm silver, 100 nM-5 μM Vitamin A, about 10 nM-1 μM Vitamin D3, about 10 nM-1 μM Vitamin K, about 100 nM-10 μM N-acetyl cysteine, and about 10 nM-500 nM Retinoic Acid.

As another illustrative example, a chemically defined media supplement is provided for supplementing a media to culture human embryonic kidney cells (HEKs), wherein the supplement may be added to a suitable cell growth medium and adds a standard concentration of ITSE (insulin, transferrin, selenium, ethanolamine), a standard concentration of Trace Elements A, about 5-100 ng/mL FGF (Fibroblast Growth Factor), about 5-100 ng/mL IGF (Insulin-like Growth Factor), about 10 nM-10 μM Cholesterol Sulfate, about 10 nM-10 μM Alpha Linolenic Acid and/or about 1 μM-1 mM Palmitoleic Acid to the medium. In further aspects, the chemically defined media supplement may further add about 5-100 ng/mL EGF (Epithelial Growth Factor), about 1 nM-1 μM Vitamin D3, about 10 nM-10 μM Ascorbyl Palmitate, about 100 nM-1 mM Oleic Acid, about 100 nM-1 mM Valproic Acid, about 100 nM-1 mM Caprylic Acid, about 1 μM-20 μM hydrocortisone, about 100-320 ppm silver, about 100 nM-5 μM Vitamin A, about 10 nM-1 μM Vitamin K, and/or about 10 nM-500 nM Thiazovivin to the medium. In other aspects, the chemically defined media supplement further adds a standard concentration of Hypoxanthine/Thymidine, about 1 μM-20 μM hydrocortisone, about 100 nM-100 μM Retinoic Acid, about 100 nM-1 mM Beta-hydroxy Butyrate, and/or about 0.5-5 g/L poloxamer-188 (PLURONIC™ F-68) to the medium.

As another illustrative example, a chemically defined media supplement is provided for supplementing a media to culture human embryonic kidney cells (HEKs), wherein the supplement may be added to a suitable cell growth medium and adds a standard concentration of ITSE (insulin, transferrin, selenium, ethanolamine), a standard concentration of Trace Elements A, about 5-100 ng/mL FGF (Fibroblast Growth Factor), about 5-100 ng/mL IGF (Insulin-like Growth Factor), about 5-100 ng/mL EGF (Epithelial Growth Factor), about 1 nM-1 µM Vitamin D3, about 10 nM-10 µM Cholesterol Sulfate, about 10 nM-10 µM Alpha Linolenic Acid, about 1 µM-1 mM Palmitoleic Acid, about 10 nM-10 µM Ascorbyl Palmitate, about 100 nM-1 mM Oleic Acid, about 100 nM-1 mM Valproic Acid, about 100 nM-1 mM Caprylic Acid, about 1 µM-20 µM hydrocortisone, a standard concentration of Hypoxanthine/Thymidine, about 100 nM-100 µM Retinoic Acid, and/or about 100 nM-1 mM Beta-hydroxy Butyrate to the medium. In various aspects, the chemically defined media supplement for HEK cells further adds to the medium about 100-320 ppm silver, 100 nM-5 µM Vitamin A, about 1 nM-1 µM Vitamin D3, about 10 nM-1 µM Vitamin K, about 0.5-5 g/L poloxamer-188 (PLURONIC™ F-68), and/or about 10 nM-500 nM Thiazovivin.

As another illustrative example, a chemically defined media supplement is provided for supplementing a media to culture smooth muscle cells (SMCs), wherein the supplement may be added to a suitable growth medium and adds a standard concentration of ITSE (insulin, transferrin, selenium, ethanolamine), a standard concentration of Trace Elements A, about 5-100 ng/mL FGF (Fibroblast Growth Factor), about 5-100 ng/mL IGF (Insulin-like Growth Factor), about 10 nm-10 µM Cholesterol Sulfate, about 10 nM-10 µM Alpha Linolenic Acid, about 1 µM-1 mM Palmitoleic Acid, about 10 nM-10 µM Ascorbyl Palmitate, and/or about 100 nM-1 mM Valproic Acid to the medium. In various aspects, the chemically defined media supplement further adds about 5-100 ng/mL EGF (Epithelial Growth Factor), about 1 nM-1 µM Vitamin D3, about 10 nM-10 µM Docosahexanoic Acid, about 100 nM-1 mM Oleic Acid, about 10 nM-10 µM N-Acetyl Cysteine, about 100-320 ppm silver, about 100 nM-5 µM Vitamin A, about 10 nM-1 µM Vitamin K, and/or about 10 nM-500 nM Retinoic Acid to the medium. In further aspects, the chemically defined media supplement may further add about 1 µM-20 µM hydrocortisone to the medium.

As another illustrative example, a chemically defined media supplement is provided for supplementing a media to culture smooth muscle cells (SMCs), wherein the supplement may be added to a suitable growth medium and adds a standard concentration of ITSE (insulin, transferrin, selenium, ethanolamine), a standard concentration of Trace Elements A, about 5-100 ng/mL FGF (Fibroblast Growth Factor), about 5-100 ng/mL IGF (Insulin-like Growth Factor), about 5-100 ng/mL EGF (Epithelial Growth Factor), about 1 nM-1 µM Vitamin D3, about 10 nM-10 µM Cholesterol Sulfate, about 10 nM-10 µM Alpha Linolenic Acid, about 1 µM-1 mM Palmitoleic Acid, about 10 nM-10 µM Ascorbyl Palmitate, about 100 nM-1 mM Valproic Acid, about 10 nM-10 µM Docosahexanoic Acid, about 100 nM-1mM Oleic Acid, about 10 nM-10 µM N-Acetyl Cysteine, and/or about 1 µM-20 µM Hydrocortisone to the medium. In various aspects, the chemically defined media supplement for culturing mesenchymal stem cells further adds to the media: 100-320 ppm silver, 100 nM-5 µM Vitamin A, about 1 nM-1 µM Vitamin D3, about 10 nM-1 µM Vitamin K, and about 10 nM-500 nM Retinoic Acid to the medium.

In any of the exemplary chemically defined media supplements may comprise each of the defined components at a concentration 100× the required concentration in the final media (e.g., the "added concentration" listed above). Accordingly, if a component is added to the media at a concentration of 100 ppm, the chemically defined media supplement comprises 10,000 ppm of that component. If the component is added at a concentration of 1 µM, the chemically defined media supplement comprises 100 µM (0.1 mM) of the component. If the component is added at a concentration of 10 µM, the chemically defined media supplement ideally comprises 1 mM of the component. If a component is added at a concentration of 100 µM, the chemically defined media supplement comprises 10 mM of the component.

Any of the chemically defined media supplements provided herein may be prepared using a suitable solvent. In various aspects, the solvent comprises water (e.g., distilled water). In various aspects, the solvent (e.g., distilled water) is initially prepared with one or more solutes and may be commercially prepared (e.g., as a stock solution) before remaining components are added. For example, in some aspects, the chemically defined media supplements comprise ITSE (insulin, transferrin, selenium, ethanolamine) at a 100× concentration. In these and related aspects, a commercially available ITSE stock solution (100×) is used as the "solvent" and other components (e.g., fatty acids, vitamins, etc) are added to it. In other aspects, (e.g., when ITSE is not part of the chemically defined media supplement), distilled water is used as the starting solvent and each component is added to it.

As noted above, the chemically defined media supplements may comprise omega 3 fatty acids (as opposed to, for example, omega 6 fatty acids). The chemically defined media supplements herein are advantageous in that they comprise high concentrations of unoxidized omega 3 fatty acids, which are typically difficult to solubilize and retain in solution in reduced form in aqueous solvents.

Cell that may be cultivated using common base media (e.g., a base media suitable for a given cell type, described below) and the chemically defined serum replacements provided herein include animal cells (e.g., insect cells, such as sf9 cells, and mammalian cells, such as human cells, chicken cells, monkey cells, etc.). In some instances, the animal cells are bovine cells, canine cells, feline cells, insect cells, avian cells, primate cells or human cells. Further, cells cultivated as set out herein may be induced pluripotent stem cells (iPSC's).

In some instances, chemically defined media supplements provided herein are used to supplement cell culture media to cultivate cells, wherein the cells are selected from the group consisting of induced pluripotent stem cells, human embryonic foreskin fibroblasts, human embryonic kidney cells (HEK) or smooth muscle cells (SMCs) or related cell types and/or cell lines.

In some instances, chemically defined media supplements may be applied to primary cells to produce new cell lines that are unaffected by exposure to animal derived culture components, and so are free of potential contamination and phenotypic changes possible due to serum exposure.

In some instances, chemically defined media supplements provided herein may be used to increase the growth (e.g., the growth rate, as compared to cell culture media compositions which omit one or more components) of cells, the viable cell density of the cell, the viral titer of a virus produced by an infected cell, or a combination thereof.

In some instances, cells cultivated using chemically defined media supplements provided herein are infected with a virus (e.g., an animal virus, a plant virus, a bacteriophage, etc.) or contain heterologous nucleic acid which encodes one or more expression product (e.g., one or more protein such as one or more cytokine, erythropoietin, antibody, etc.) for which production is desired. In some instances, cells cultivated using chemically defined serum substitutes are used to produce iPSC's. In some instances, these stem cells may be used to produce therapies such as organs (e.g., Larynx, skin) for transplant. In some instances, stem cells cultured using chemically defined serum substitutes may be used for production of other cell types for above mentioned purposes (e.g., vaccine production, protein production). In some instances, cells produced using chemically defined serum substitutes may be used for medical testing and research.

Chemically defined media supplements provided herein may be added to basal media to culture cells (e.g., kidney cells, WI-38 cells and MRC-5 cells and others) capable of producing proteins, vaccines, viruses, viral particles, viral proteins or nucleic acids, and/or a viral fragments. "Basal Media" as used herein is described below but in general refers to a base media available for given cell types (e.g., minimum essential medium (MEM), Dubelco's minimum essential medium (DMEM), or Essential 8 Media, all provided by Gibco). In many instances, such cells are cultured under serum-free conditions, but chemically defined conditions are indicated for these purposes.

Further provided herein are methods for culturing a cell population (e.g., a diploid cell population), comprising incubating the cell population in a cell culture medium supplemented with a chemically defined media supplement as defined herein. In some instances, such methods comprises vaccine producing cells (e.g., HEK, WI-38, MRC-5)), where the method comprising incubating the cell population in chemically defined cell culture conditions comprising: (i) a cyclodextrin or other carrier (e.g., methylated cyclodextrin, ascorbic acid) at least one or more polyunsaturated fatty acids, such as one or more of the following: docosahexanoic acid, eicosapentanoic acid, oleic acid, palmitic acid, palmitoleic acid, caprylic acid, alpha linolenic acid and a cholesterol, as well as suitable dilution of other hydrophobic nutrients and trace elements known to be provided by serum as presented in table 1, and growth factors including fibroblast growth factor (e.g. FGF, bFGF), epithelial growth factor (EGF), and insulin-like growth factor (IGF).

In some instances, synthetic growth factors, or growth factor analogs may be used to avoid animal sourcing. Components used for cell-type specific supplements will be selected according to increases in viable cell density in resulting chemically defined cell culture medium compared to a viable cell density in a serum-containing medium without further supplementation.

In some instances, methods for culturing a cell population (e.g., a stem cell population) include instances where: (i) the medium or supplement increases: the growth of the cell, the viable cell density of the cell, the viral titer of a virus infected cell, or a combination thereof; and/or, (ii) the cell (e.g., HEK cell) is capable of producing a vaccine, a virus, a viral particle, a viral protein or nucleic acid, or a viral fragment thereof under chemically defined conditions. Further, in some instances: (i) the virus is an animal virus, a plant virus or a bacteriophage; and/or, (ii) the virus is selected from the group consisting of Coronavirus, Varicella zoster virus (VZV), Rubella, Measles, Mumps, Hepatitis A, Adenovirus, Poliomyelitis, Rotavirus, Smallpox, Chickenpox, Yellow fever, Papillomavirus, Ebola virus, HIV, Rabies or vesicular stomatitis virus (VSV), and Dengue virus.

In some instances, the cell population cultivated using compositions and methods provided herein are selected from the group consisting of induced pluripotent stem cells (iPSCs), HEK 293 cells, HFF1 cells, MRC-5 cells, MRC-5 RCB cells, MRC-9 cells, WI-38 cells, 2BS cells, Walvax-2 cells, IMR-90 cells, IMR-91 cells, KMB-17 cells, HUT series cell, VERO cells, and any clone of these cells.

Further provided herein are combinations comprising a suitable dilution of the chemically defined media supplements provided herein. In some instances of such combinations (i) the cell is a primary mammalian cell; and/or, (ii) the cell is a bovine cell, a feline cell, an insect cell, an avian cell, a primate cell or a human cell; and/or, (iii) the animal cell is a diploid cell; and/or (iv) the cell is selected from the group consisting of. induced pluripotent stem cells (iPSCs), HEK 293 cells, HFF1 cells, MRC-5 cells, MRC-5 RCB cells, MRC-9 cells, WI-38 cells, 2BS cells, Walvax-2 cells, IMR-90 cells, IMR-91 cells, KMB-17 cells, HUT series cell, VERO cells, and any clone of these cells.

In some instances, the cells (e.g., HEK cells, WI-38 cells) produce a vaccine, a virus, a viral particle, a viral protein or nucleic acid, or a viral fragment under serum-free conditions. In some instances. the cells cultured using the chemically defined serum replacements may be used for therapies, production of protein for human consumption, drug testing or research.

In an aspect, provided herein are methods for preferentially expanding members of a cell subpopulation (e.g., a mononuclear cell population). Such methods comprise exposing a mixed population of cells (e.g., iPSC cells) to: (i) cyclodextrin, or other carrier; (ii) fatty acids, (iii) bioactive molecules, and/or (iv) growth factors. In some embodiments, the molar ratio of two or more nutrients or small molecules is adjusted to induce the members of the cell subpopulation (e.g., a mononuclear cell subpopulation) to preferentially expand over members of other cell subpopulations (e.g., one of more other mononuclear cell subpopulations) or iPSCs.

Embodiments of the present invention include unique and complete mixes of hydrophobic nutrients, which support the specific cell types in chemically defined conditions when used with most available basal media. As used herein, "basal media" refers to any standard media used by one of skill in the art to culture cells. Preferably, the "basal media" is serum free and does not comprise any animal-derived products. As an example, the "basal media" that may be supplemented using compositions described herein may comprise minimum essential medium (MEM). For example, the basal media may comprise Dulbecco's minimum essential medium (DMEM), Dulbecco's Modified Eagle Medium: Nutrient Mixture F-12 (DMEM/F12). In other examples, the basal media may comprise Essential 8 Media (Gibco).

III. Methods

Further aspects of the present disclosure are directed to methods of using any of the media supplements provided above. In various aspects, the methods comprise adding a suitable amount of the chemically defined media supplement to a media used to culture a desired cell type, such that the concentrations of each component in the media reach the desired concentrations listed above. In aspects, the methods may further comprise culturing a cell in the supplemented media.

In further aspects of the present disclosure, a method of culturing a cell is provided, the method comprising adding to a cell culture medium a chemically defined media supplement of described herein and culturing the cell in the cell culture medium.

In various aspects, the cell is an induced pluripotent stem cell, and the chemically defined media supplement comprises ascorbyl palmitate, docosahexanoic acid and cholesterol sulfate.

In other aspects, the cell is a human foreskin fibroblast (HFF), and the chemically defined media supplement comprises ITSE (Insulin, transferrin, selenium, ethanolamine), Trace Elements A, Alpha Linolenic Acid, fibroblast growth factor, insulin-like growth factor, oleic acid, Vitamin D3, and docosahexanoic acid. In some aspects, the chemically defined media supplement further comprises epithelial growth factor (EGF), vitamin D3, palmitoleic acid, ascorbyl palmitate, cholesterol, silver, vitamin A, vitamin D3, vitamin K, N-acetyl cysteine, retinoic acid or a combination of any of two or more thereof. In still further aspects, the chemically defined media supplement further comprises hydrocortisone.

In still other aspects, the cell is a human embryonic kidney (HEK) cell, and the chemically defined media supplement comprises ITSE (Insulin, transferrin, selenium, ethanolamine), Trace Elements A, alpha linolenic acid, fibroblast growth factor (FGF), insulin-like growth factor (IGF) cholesterol sulfate and palmitoleic acid. In various aspects, the chemically defined media supplement further comprises epithelial growth factor (EGF), Vitamin D3, ascorbyl palmitate, oleic acid, valproic acid, caprylic acid, hydrocortisone, vitamin A, vitamin D3, vitamin K, or a combination of any two or more thereof. Optionally, the chemically defined media supplement may further comprise hydrocortisone, hypoxanthine/thymidine, retinoic acid, beta-hydroxy butyrate, poloxamer-188 or a combination of any two or more thereof.

In still other aspects, the cell is a smooth muscle cell (SMC) and the chemically defined media supplement comprises ITSE (Insulin, transferrin, selenium, ethanolamine), Trace Elements A, alpha linolenic acid, fibroblast growth factor, insulin-like growth factor, cholesterol sulfate, palmitoleic acid, ascorbyl palmitate, and valproic acid. In various aspects, the chemically defined media supplement further comprises comprising epithelial growth factor (EGF), vitamin D3, docosahexanoic Acid, oleic acid, N-acetyl cysteine, silver, vitamin A, vitamin K, retinoic acid or a combination of any two or more thereof. In various aspects, the chemically defined media supplement further comprises hydrocortisone.

Having described several embodiments, it will be recognized by those skilled in the art that various modifications, alternative constructions, and equivalents may be used without departing from the spirit of the present inventive concept. Additionally, a number of well-known processes and elements have not been described in order to avoid unnecessarily obscuring the present inventive concept. Accordingly, this description should not be taken as limiting the scope of the present inventive concept.

Those skilled in the art will appreciate that the presently disclosed embodiments teach by way of example and not by limitation. Therefore, the matter contained in this description or shown in the accompanying drawings should be interpreted as illustrative and not in a limiting sense. The following claims are intended to cover all generic and specific features described herein, as well as all statements of the scope of the method and assemblies, which, as a matter of language, might be said to fall there between.

EXAMPLES

The following examples are included to demonstrate preferred embodiments of the disclosure. It should be appreciated by those of skill in the art that the techniques disclosed in the examples that follow represent techniques discovered by the inventor to function well in the practice of the present disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the present disclosure.

Example 1

The following media supplements were prepared for use in the subsequent examples. In brief, lipophilic elements (e.g., fatty acids, cholesterol) were solubilized in an aqueous buffer (e.g., ITSE for FiboPur or HEKPur or distilled water for StemPur). Further hydrophilic elements were then added to the mixture to produce the final supplement. Each supplement was prepared at 100× concentration to achieve the range of concentrations in the media as described in Tables 3 to 6.

TABLE 3

Fibroblast supplement FibroPur™

| Component (each at 100× in supplement) | Targeted Concentration Range in Media |
|---|---|
| ITSE (Insulin-Transferrin-Selenium-Ethanolamine) | 1× |
| Trace Elements A | 1× |
| Alpha Linolenic Acid | 10 nM-10 μM |
| Docosahexanoic Acid | 10 nM-10 μM |
| Oleic Acid | 1 nM-1 μM |
| FGF (Fibroblast Growth Factor) | 5-100 ng/mL |
| IGF (Insulin-like Growth Factor) | 5-100 ng/mL |
| EGF (Epithelial Growth Factor) | 5-100 ng/mL |
| Palmitoleic Acid | 1 nM-10 μM |
| Ascorbyl Palmitate | 10 nM-10 μM |
| Cholesterol Sulfate | 10 nM-10 μM |
| Hydrocortisone | 1 μM-20 μM |

TABLE 4

HEK supplement HEKPur™

| Component (each at 100× in supplement) | Targeted Concentration Range in Media |
|---|---|
| ITSE (Insulin-Transferrin-Selenium-Ethanolamine) | 1× |
| Trace Elements A | 1× |
| FGF (Fibroblast Growth Factor) | 5-100 ng/mL |
| IGF (Insulin-like Growth Factor) | 5-100 ng/mL |
| EGF (Epithelial Growth Factor) | 5-100 ng/mL |
| Cholesterol Sulfate | 10 nM-10 μM |
| Alpha Linolenic Acid | 10 nM-10 μM |
| Palmitoleic Acid | 1 μM-1 mM |
| Ascorbyl Palmitate | 10 nM-10 μM |
| Oleic Acid | 100 nM-1 mM |
| Hydrocortisone | 1 μM-20 μM |

TABLE 5 iPSC Supplement StemPur™

| Component | Targeted Concentration Range in Media |
|---|---|
| Ascorbyl Palmitate | 1 μM-1 mM |
| Docosahexanoic Acid | 1 nM-10 μM |
| Cholesterol Sulfate | 10 nM-10 μM |
| Palmitoleic Acid | 100 nM-10 μM |
| Ascorbic Acid | 1 μM-1 mM |

TABLE 5-continued iPSC Supplement StemPur™

| Component | Targeted Concentration Range in Media |
| --- | --- |
| Oleic Acid | 10 nM-10 μM |
| Alpha Linolenic Acid | 10-nM-1 μM |

TABLE 6

SMC Supplement

| Component | Targeted Concentration Range in Media |
| --- | --- |
| ITSE (Insulin-Transferrin-Selenium-Ethanolamine) | 1× |
| Trace Elements A | 1× |
| FGF (Fibroblast Growth Factor) | 5-100 ng/mL |
| IGF (Insulin-like Growth Factor) | 5-100 ng/mL |
| EGF (Epitheilial Growth Factor) | 5-100 ng/mL |
| Cholesterol Sulfate | 10 nM-10 μM |
| Alpha Linolenic Acid | 10 nM-10 μM |
| Palmitoleic Acid | 1 μM-1 mM |
| Ascorbyl Palmitate | 10 nM-10 μM |
| Docosahexanoic Acid | 10 nM-10 μM |
| Oleic Acid | 100 nM-1 mM |
| Hydrocortisone | 1 μM-20 μM |

Example 2

Cells were grown in 12 well tissue culture treated plates with no matrix. Cells were plated at a density of 5×10⁴ cells/well and passaged using trypsin at day 4 and day 7, with counting done on day 10. Cells were directly adapted to experimental conditions and grown at 37° Celsius in a humidified incubator at 5% $O_2$, with media changed every two days. FIG. 1 is a graph illustrating the effect of fibroblast supplement FibroPur™ comprising ITSE (Insulin-Transferrin-Selenium-Ethanolamine), Trace Elements A, Alpha Linolenic Acid, Docosahexanoic Acid, Oleic Acid, FGF (Fibroblast Growth Factor), IGF (Insulin-like Growth Factor), EGF (Epithelial Growth Factor), palmitoleic acid, ascorbyl palmitate, cholesterol sulfate, hydrocortisone on proliferation of fibroblasts in DMEM as compared to the effect of serum. The supplement was prepared to deliver a concentration of each component to the culture medium as indicated in Table 3.

Example 3

Figure 2:
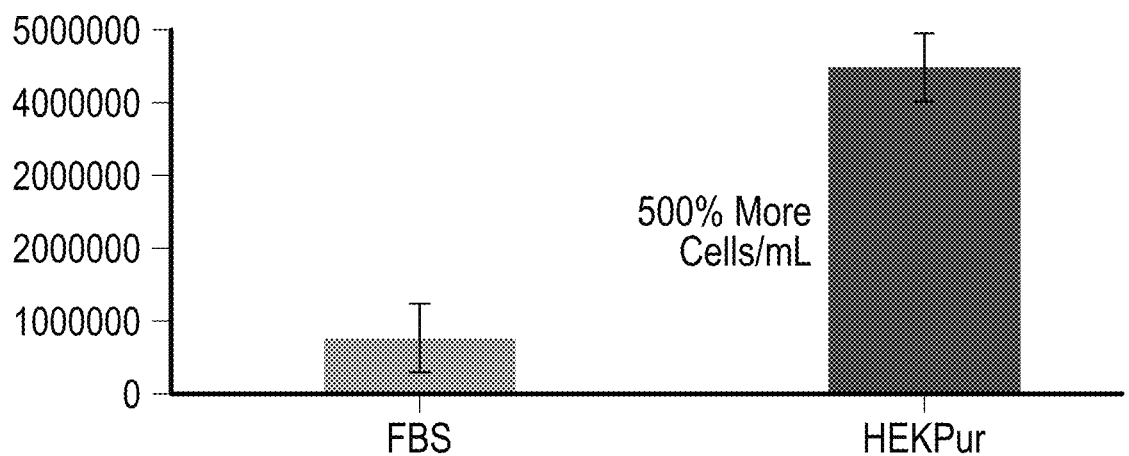
FIG. 2 shows proliferation and standard deviation of HEK cells grown in DMEM medium supplemented with optimized chemically defined supplement, compared to supplementation with FBS. Counted day 10.

Cells were grown in 12 well tissue culture treated plates with no matrix. Cells were plated at a density of 5×10⁴ cells/well, using thiazovivin for passaging support, and passaged without trypsin at day 5 with counting done on day 10. Cells were directly adapted to experimental conditions and grown at 37° C. Celsius in a humidified incubator at 5% $O_2$, with media changed every two days. FIG. 2 shows the effect of HEKPur™ supplement comprising ITSE (Insulin-Transferrin-Selenium-Ethanolamine), Trace Elements A, FGF (Fibroblast Growth Factor), IGF (Insulin-like Growth Factor), EGF (Epithelial Growth Factor), cholesterol sulfate, alpha linolenic acid, palmitoleic acid, ascorbyl palmitate, oleic acid and hydrocortisone on HEK cell proliferation in DMEM as compared to the effect of serum. The supplement was prepared to deliver a concentration of each component to the culture medium as indicated in Table 4.

Example 4

Figure 3:
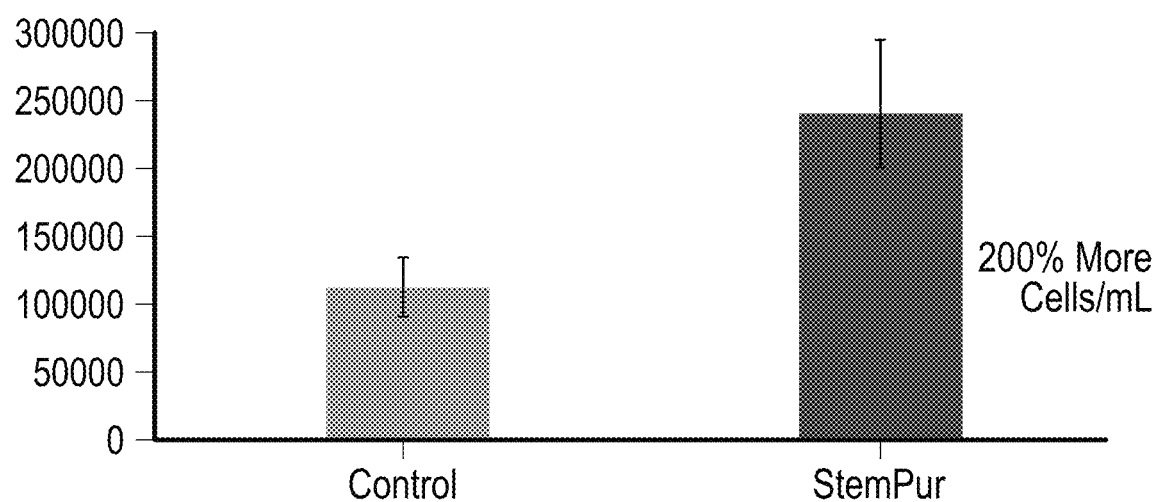
FIG. 3 shows proliferation and standard deviation of Cy2 iPSC cells grown in Essential 8 medium supplemented with optimized chemically defined supplement, compared to supplementation with FBS. Counted day 10.

Cells were grown in 12 well tissue culture treated plates with Vitronectin matrix. Cells were plated at a density of 5×10⁴ cells/well, using thiazovivin for initial seeding support, and passaged using VERSENE™ at day 5 with counting done on day 10. Cells were directly adapted to experimental conditions and grown at 37® Celsius in a humidified incubator at 5% $O_2$, with media changed every day. FIG. 3 shows the effect of StemPur™ supplement comprising ascorbyl palmitate, docosahexanoic acid, cholesterol sulfate, palmitoleic acid, ascorbic acid, oleic acid and alpha linolenic acid on iPSC cell proliferation in DMEM as compared to the effect of serum. The supplement was prepared to deliver a concentration of each component to the culture medium as indicated in Table 5.

Example 5

Figure 4:
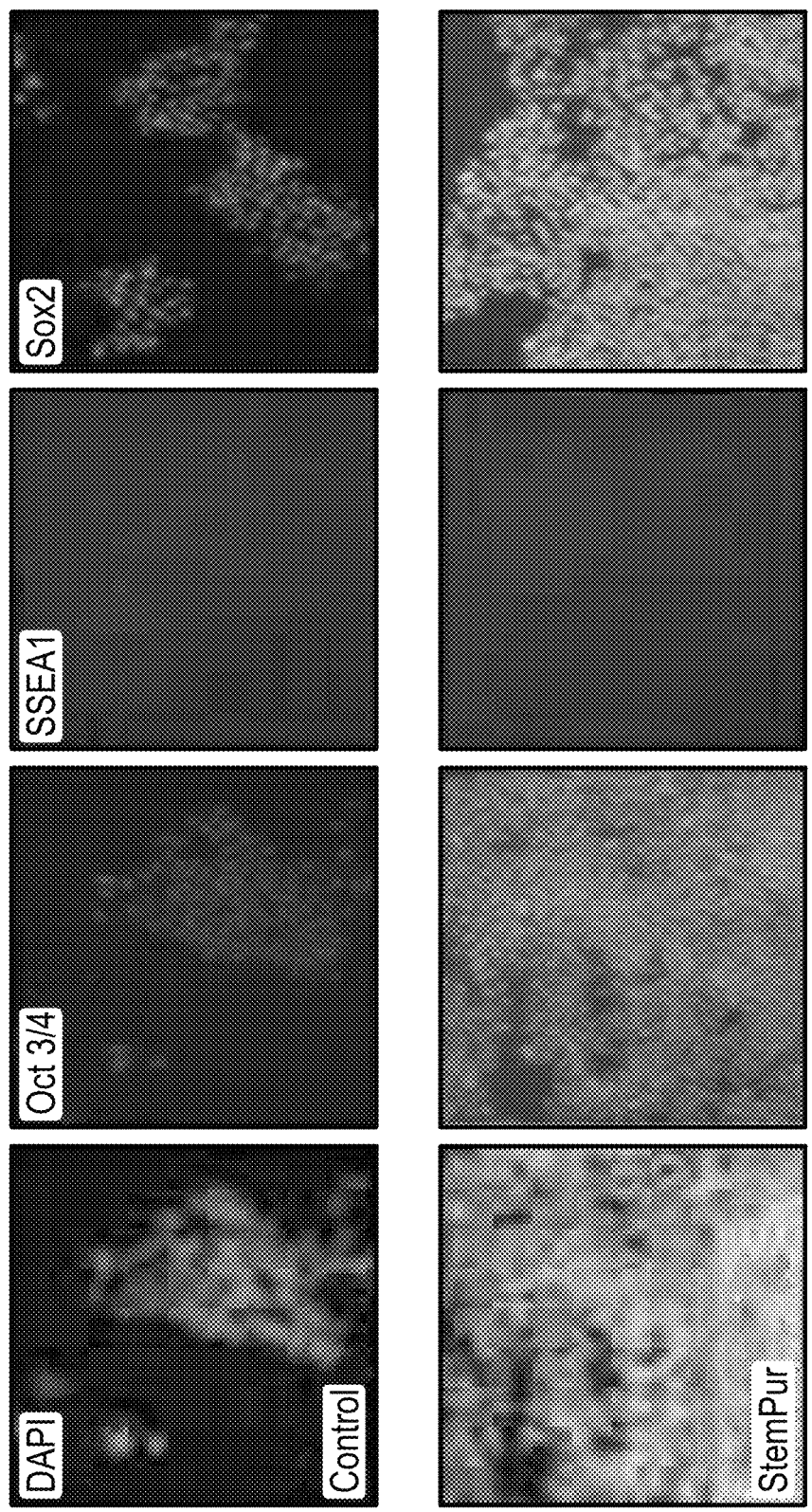
FIG. 4 shows fluorescent imaging of cells grown in Essential 8 media, and in Essential 8 with StemPur supplement. Oct3/4 and SOX2 are positive indicators of pluripotency. SSEA1 is a negative indicator of pluripotency, or indicator of differentiation (loss of pluripotency). Cells grown with StemPur exhibited stronger pluripotency signals.

Cells were grown in 12 well tissue culture treated plates with Vitronectin matrix at 37® Celsius in a humidified incubator at 5% $O_2$, with media changed every day. Cells were grown in experimental and untreated media for 14 days and passaged using VERSENE™ at day 5 and day 10. At day 14, cells were fixed and stained using Alexa Fluor conjugated stains, and viewed/photographed using a confocal microscope. FIG. 4 shows the result of a staining assay that is specific to certain proteins produced by cells that indicate level of pluripotency or "sternness". Besides proliferation, the pluripotency of a population of stem cells can be affected by certain nutrients. This test illustrated that StemPur™ supplement (defined above in Example 4 and Table 5) supports maintenance of pluripotency as well as cell proliferation

Example 6

Figure 5:
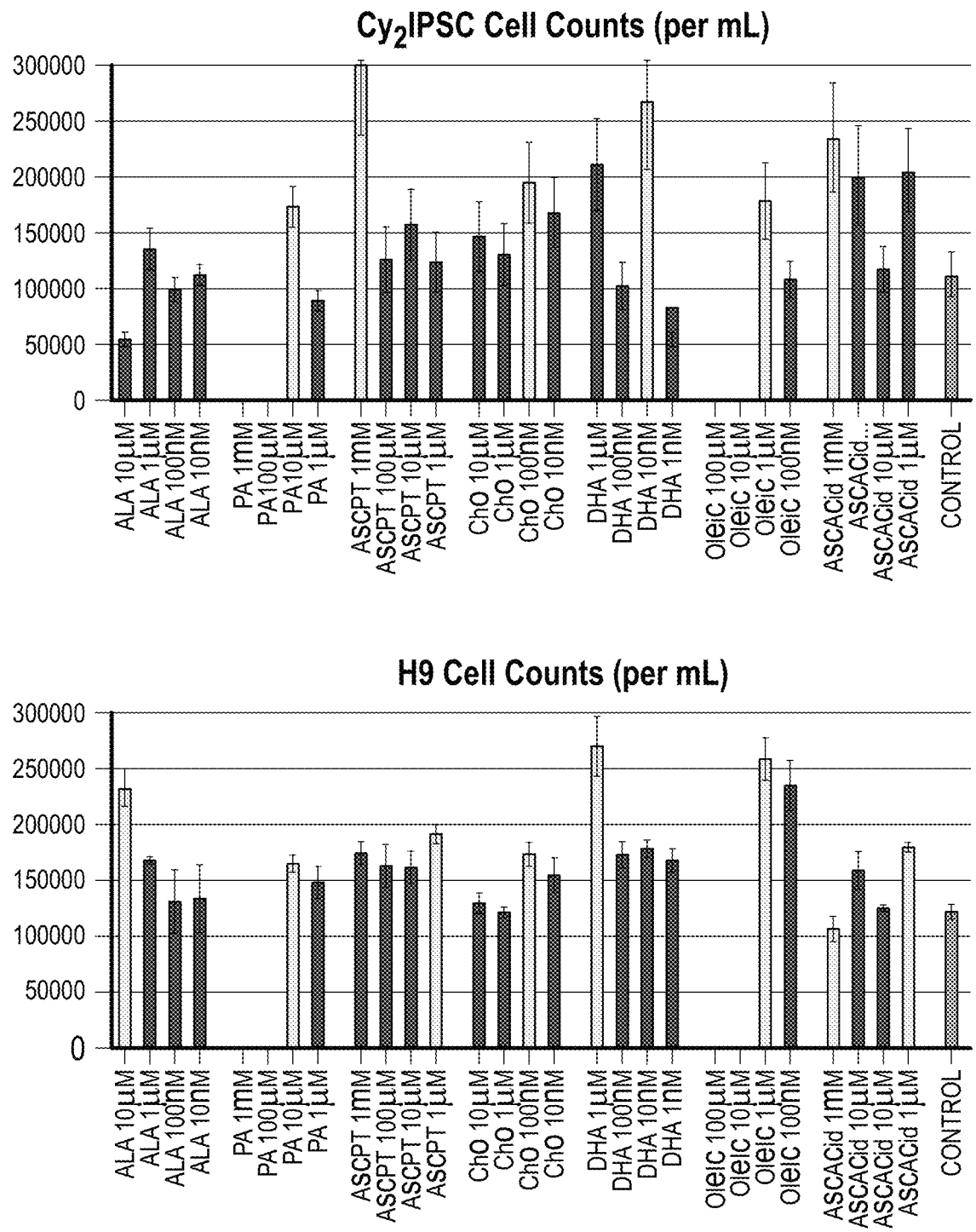
FIG. 5 shows the serial dilution of individual lipids in increasing concentration on two different types of stem cells: iPSC and embryonic stem cells. These cells are known to have certain biological and epigenetic differences which have been difficult to identify. Significant differences in reaction to certain lipids may indicate metabolic and energetic differences.

Cells were grown in 12 well tissue culture treated plates with Vitronectin matrix. Cells were plated at a density of 5×10⁴ cells/well, using thiazovivin for initial seeding support and passaged using VERSENE™ at day 5 with counting done on day 9. Cells were directly adapted to experimental conditions and grown at 37° C. Celsius in a humidified incubator at 5% $O_2$, with media changed every day. Experimental conditions consisted of serial dilution of individual lipids alone, and comparison made with supplementation with Fetal Bovine Serum (FBS) determined by live cell counts. Identical conditions were applied to iPSC's and embryonic stem cells. FIG. 5 shows the serial dilution of individual lipids in increasing concentration on two different types of stem cells: iPSC and embryonic stem cells. These cells are known to have certain biological and epigenetic differences which have been difficult to identify. Significant differences in reaction to certain lipids may indicate metabolic and energetic differences.

Example 7

Figure 6:
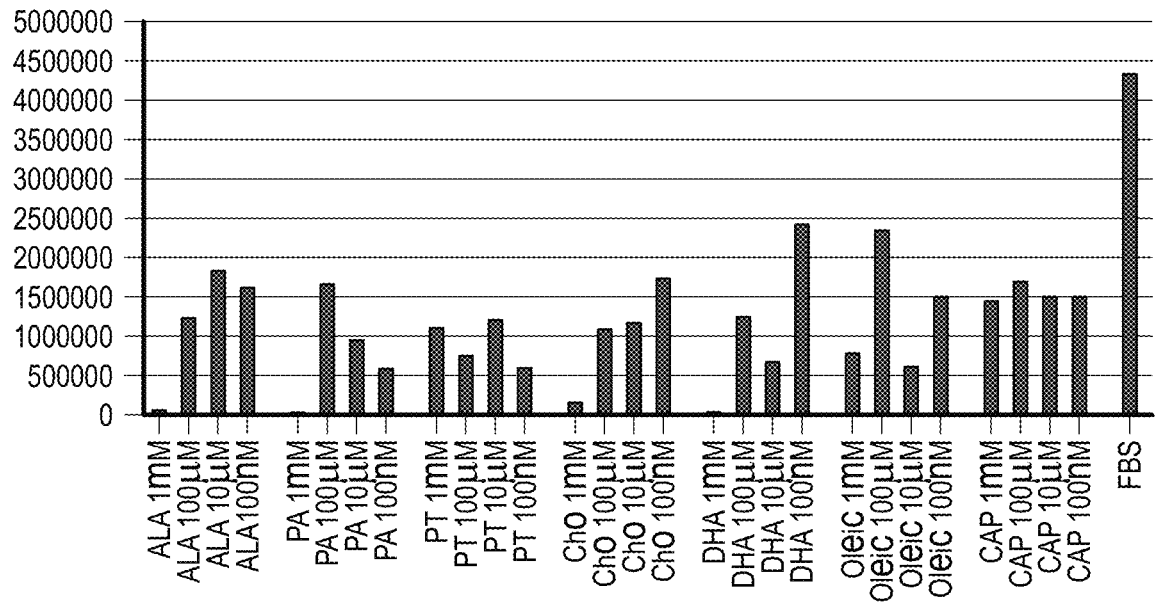
FIG. 6 shows the serial dilution of individual lipids in increasing concentration on two different cell types—muscle cells (myocytes) and kidney cells (HEK). This illustrates the need for specific supplements for different cell types.
Figure 6:
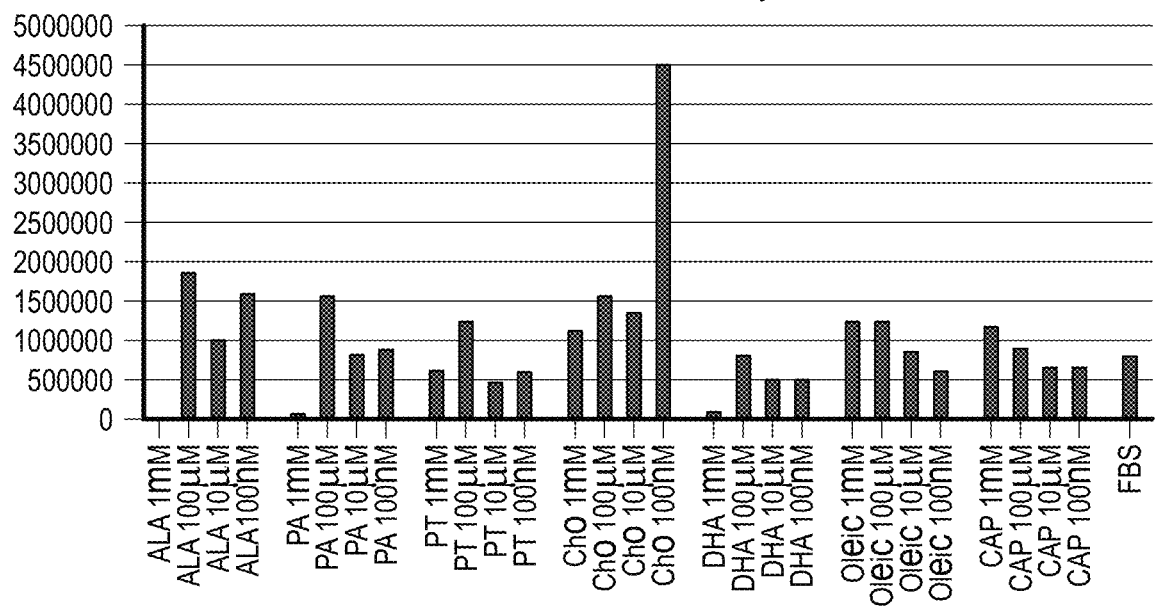

Cells were grown in 12 well tissue culture treated plates with no matrix. Cells were plated at a density of 5×10⁴ cells/well and passaged using VERSENE™ at day 5 with counting done on day 9. Cells were directly adapted to experimental conditions and grown at 37° C. Celsius in a humidified incubator at 5% $O_2$, with media changed every two days. Experimental conditions consisted of serial dilution of individual lipids alone, and comparison made with supplementation with Fetal Bovine Serum (FBS) determined by live cell counts. Identical conditions were applied to Myocytes and HEK (kidney) cells. FIG. 6 shows the serial dilution of individual lipids in increasing concentration on two different cell types—muscle cells (myocytes) and kidney cells (HEK). This illustrates the need for specific supplements for different cell types.

Example 8

Solubilized lipids were evaluated by spectrophotometric assay using Phenolphthalein, which is known to occupy the complexing reagents used for five hydrophobic nutrients used in chemically defined mixes. Phenolphthalein is known to be displaced from the reagent when a hydrophobic moiety is complexed, so the concentration of occupied reagents was extrapolated from coloration indicating concentration of free phenolphthalein in solution when a known amount of solubilized nutrient was dosed with a known quantity of Phenolphthalein. One nutrient (oleic acid; OA) was known to be incomplete in its solubilization, and the assay confirms this, by reporting a lower amount of free phenolphthalein, indicating a greater number of free reagent, and therefore a free lipid concentration greater than the literature level. FIG. 7 shows the result of a spectrophotometric assay using phenolphthalein indicator to determine the complexation of efficiency of 5 lipids complexed with cyclodextrins. Phenolphthalein is colored when free in solution at pH 8+. It readily complexes with cyclodextrins of all types and is colorless when complexed. It is preferentially displaced by more hydrophobic molecules, so when added to a known concentration of complexed lipids, the absorbance can determine how much free phenolphthalein is present, and therefore how many free cyclodextrins are present. Since the stoichiometry of mixing is 1:1, the concentration of cyclodextrins that are free to interact with Phenolphthalein logically equals the concentration of free lipid in solution. With one exception, this concentration is below the critical micelle concentration of each fatty acid. The exception is oleic acid, which was cloudy when tested, and so was known to be incompletely complexed.

Example 9

Optimization of mixes is achieved using Design of Experiments (DoE) computer-based design and analysis protocols. Experiments are computer designed according to number of variables to test, and serial dilutions of those variables. Results are able to indicate two factor interactions. The plane of the graph is the resulting cell count, and the third dimension shows how increase of one component is related to increase or decrease of another. This enables the optimization of many interdependent nutrients using maxima and repeat application.

FIG. 8 shows results from DoE output show maxima and minima relating to two or more factors, as indicated. These DoE data show two-factor interaction results on HFF cells. Vertical axes reflect cell numbers/mL after culture for 5 days. Horizontal axes correspond to increasing concentration of indicated lipids. FIG. 8A shows the agonistic relationship between PA (palmitoleic acid) and PT (palmitate), while FIG. 8B shows the antagonist relationship between PA and α linolenic acid (ALA).

Example 10

Experiments described in Examples 2-6 and Design of Experiments (DoE) experiments, as described in Example 9, were done for various combinations of components for each optimized chemically defined media supplement. Based on the results of these experiments, the following components were added to each media supplement (as provided in Tables 3-6 above). These DoE experiments were also used to categorize components as described in Tables A, B and C above. Exemplary concentrations of each component, based on target ranges of concentrations in the final media, may be determined generally as provided in Table D or the Tables 7-10 below.

TABLE 7

Fibroblast supplement - Added Components (See Table 3)

| Component (each at 100× in supplement) | Targeted Concentration Range in Media |
| --- | --- |
| Vitamin D3 | 1 nM-1 µM |
| Silver | 100-320 ppm |
| Vitamin A | 100 nM-5 µM |
| Vitamin K | 10 nM-1 µM |
| N-Acetyl Cysteine | 100 nM-10 µM |
| Retinoic Acid | 10 nM-500 nM |

TABLE 8

HEK supplement Added Components (see Table 4)

| Component (each at 100× in supplement) | Targeted Concentration Range in Media |
| --- | --- |
| vitamin D3 | 1 nM-1 µM |
| valproic acid | 100 nM-1 mM |
| capryllic acid | 100 nM-1 mM |
| hypoxanthine/thymidine | 1× (Standard Concentrations) |
| retinoic acid | 100 nM-100 µM |
| beta-hydroxy butyrate | 100 nM-1 mM |
| silver | 100-320 ppm |
| vitamin A | 100 nM-5 µM |
| vitamin K | 10 nM-1 µM |
| poloxamer-188 | 0.5-5 g/L |
| thiazovivin | 10 nM-500 nM |

TABLE 9 iPSC Supplement StemPur Added Components (see Table 5)

| Component | Targeted Concentration Range in Media |
| --- | --- |
| silver | 100-320 ppm |
| vitamin A | 50-200 nM |
| vitamin D3 | 10 nM-200 nM |
| vitamin K | 10 nM-1 microM |

TABLE 10

SMC Supplement Added Components (see Table 7)

| Component | Targeted Concentration Range in Media |
| --- | --- |
| vitamin D3 | 1 nM-1 µM |
| valproic acid | 100 nM-1 mM |
| N-acetyl cysteine | 10 nM-10 µM |
| silver | 100-320 ppm |
| vitamin A | 100 nM-5 µM |
| vitamin K | 10 nM-1 µM |
| retinoic acid | 10 nM-500 nM |

What is claimed is:

1. A chemically defined media supplement comprising:
   (a) Ascorbyl palmitate, docosahexanoic acid, palmitoleic acid, cholesterol sulfate and at least two components selected from the group consisting of ascorbic acid, silver, vitamin A, vitamin D3, and vitamin K; or
   (b) ITSE (Insulin, transferrin, selenium, ethanolamine), Trace Elements A, Alpha Linolenic Acid, fibroblast growth factor, insulin-like growth factor, oleic acid, docosahexanoic acid, and vitamin D3; or
   (c) ITSE (Insulin, transferrin, selenium, ethanolamine), Trace Elements A, Alpha Linolenic Acid, fibroblast growth factor, insulin-like growth factor, cholesterol sulfate and palmitoleic acid;
   wherein the chemically defined media supplement is animal derived product free.

2. The chemically defined media supplement of claim 1, comprising (a).

3. The chemically defined media supplement of claim 2 further comprising oleic acid, alpha linolenic acid or both oleic acid and alpha linolenic acid.

4. The chemically defined media supplement of claim 1, comprising (b).

5. The chemically defined media supplement of claim 4 further comprising epithelial growth factor (EGF), vitamin D3, palmitoleic acid, ascorbyl palmitate, cholesterol, silver, vitamin A, vitamin D3, vitamin K, N-acetyl cysteine, retinoic acid or any of a combination of any two or more thereof.

6. The chemically defined media supplement of claim 5, further comprising hydrocortisone.

7. The chemically defined media supplement of claim 1, comprising (c).

8. The chemically defined media supplement of claim 7, further comprising epithelial growth factor (EGF), Vitamin D3, ascorbyl palmitate, oleic acid, valproic acid, caprylic acid, hydrocortisone, vitamin A, vitamin D3, vitamin K, or a combination of any two or more thereof.

9. The chemically defined media supplement of claim 8, further comprising hydrocortisone, hypoxanthine/thymidine, retinoic acid, beta-hydroxy butyrate, poloxamer-188 or a combination of any two or more thereof.

10. The chemically defined media supplement of claim 7, further comprising ascorbyl palmitate, and valproic acid.

11. The chemically defined media supplement of claim 10, further comprising epithelial growth factor (EGF), vitamin D3, docosahexanoic Acid, oleic acid, N-acetyl cysteine, silver, vitamin A, vitamin K, retinoic acid or a combination of any two or more thereof.

12. The chemically defined media supplement of claim 11, further comprising hydrocortisone.

13. The chemically defined media supplement of claim 1 comprising:
   (a) ascorbyl palmitate, docosahexanoic acid, cholesterol sulfate, palmitoleic acid, ascorbic acid, silver, vitamin A, vitamin D3, vitamin K, oleic acid and alpha linolenic acid; or
   (b) ITSE (insulin, transferrin, selenium, ethanolamine), Trace Elements A, alpha linolenic acid, docosahexanoic acid, oleic acid, FGF (fibroblast growth factor), IGF (insulin-like growth factor), vitamin D3, EGF (epithelial growth factor), palmitoleic acid, ascorbyl palmitate, cholesterol sulfate, silver, vitamin A, vitamin K, N-acetyl cysteine, retinoic acid and hydrocortisone; or
   (c) ITSE (insulin, transferrin, selenium, ethanolamine), Trace Elements A, FGF (fibroblast growth factor), IGF (insulin-like growth factor), cholesterol sulfate, alpha linolenic acid, palm itoleic acid, EGF (epithelial growth factor), vitamin D3, ascorbyl palmitate, oleic acid, valproic acid, caprylic acid, hydrocortisone, silver, vitamin A, vitamin K, thiazovivin, hypoxanthine/thymidine, hydrocortisone, retinoic acid, beta-hydroxy butyrate, and poloxamer-188; or
   (d) ITSE (insulin, transferrin, selenium, ethanolamine), Trace Elements A, FGF (fibroblast growth factor), IGF (insulin-like growth factor, cholesterol sulfate, an alpha linolenic acid, palmitoleic acid, ascorbyl palmitate, valproic acid, EGF (epithelial growth factor), vitamin D3, docosahexanoic acid, oleic acid, N-acetyl cysteine, silver, vitamin A, vitamin K, retinoic acid, and hydrocortisone.

14. The chemically defined media supplement of claim 1, wherein the chemically defined media supplement does not comprise albumin.

15. The chemically defined media supplement of claim 1, wherein the supplement is used to supplement a culture media for induced pluripotent stem cells (iPSCs), human foreskin fibroblasts (HFF), human embryonic kidney (HEK) cells, or smooth muscle cells (SMCs).

16. A method of culturing a cell, comprising adding to a cell culture medium a chemically defined media supplement of claim 1 and culturing the cell in the cell culture medium.

17. The method of claim 16, wherein the cell is an induced pluripotent stem cell, and the chemically defined media supplement comprises ascorbyl palmitate, docosahexanoic acid and cholesterol sulfate.

18. The method of claim 16, wherein:
   (a) the cell is a human foreskin fibroblast (HFF), and the chemically defined media supplement comprises ITSE (Insulin, transferrin, selenium, ethanolamine), Trace Elements A, Alpha Linolenic Acid, fibroblast growth factor, insulin-like growth factor, oleic acid, Vitamin D3, and docosahexanoic acid; or
   (b) the cell is a human embryonic kidney (HEK) cell, and the chemically defined media supplement comprises ITSE (Insulin, transferrin, selenium, ethanolamine), Trace Elements A, alpha linolenic acid, fibroblast growth factor (FGF), insulin-like growth factor (IGF) cholesterol sulfate and palm itoleic acid; or
   (c) the cell is a smooth muscle cell (SMC) and the chemically defined media supplement comprises ITSE (Insulin, transferrin, selenium, ethanolamine), Trace Elements A, alpha linolenic acid, fibroblast growth factor, insulin-like growth factor, cholesterol sulfate, palmitoleic acid, ascorbyl palmitate, and valproic acid.

* * * * *